(12) United States Patent
Strongin et al.

(10) Patent No.: US 10,773,238 B2
(45) Date of Patent: Sep. 15, 2020

(54) ENRICHMENT OF LYSOPHOSPHATIDIC ACIDS WITH TEMPLATED POLYMERIC MATERIALS

(71) Applicant: Portland State University, Portland, OR (US)

(72) Inventors: Robert M. Strongin, Portland, OR (US); Martha Sibrian-Vazquez, Portland, OR (US); Jialu Wang, Portland, OR (US); Jorge O. Escobedo-Cordova, Portland, OR (US)

(73) Assignee: Portland State University, Portland, OR (US)

(*) Notice: Subject to any disclaimer, the term of this patent is extended or adjusted under 35 U.S.C. 154(b) by 369 days.

(21) Appl. No.: 15/553,947

(22) PCT Filed: Feb. 23, 2016

(86) PCT No.: PCT/US2016/019072
§ 371 (c)(1),
(2) Date: Aug. 25, 2017

(87) PCT Pub. No.: WO2016/137953
PCT Pub. Date: Sep. 1, 2016

(65) Prior Publication Data
US 2018/0071716 A1  Mar. 15, 2018

Related U.S. Application Data

(60) Provisional application No. 62/126,208, filed on Feb. 27, 2015.

(51) Int. Cl.
*B01D 15/32* (2006.01)
*B01D 15/42* (2006.01)
(Continued)

(52) U.S. Cl.
CPC .......... *B01J 20/268* (2013.01); *B01D 15/325* (2013.01); *B01D 15/426* (2013.01); *B01J 20/281* (2013.01);
(Continued)

(58) Field of Classification Search
CPC ...... B01J 20/268; B01J 20/281; B01J 20/285; B01J 20/3057; B01J 2220/4812;
(Continued)

(56) References Cited

U.S. PATENT DOCUMENTS

2005/0276781 A1  12/2005  Ross et al.

FOREIGN PATENT DOCUMENTS

| WO | WO 2009/064245 | 5/2009 |
| WO | WO 2014/177856 | 11/2014 |
| WO | WO 2015/122845 A1 | 8/2015 |

OTHER PUBLICATIONS

Ochoa, Cris, "Synthesis of templated polymeric materials for plasma LPA enrichment", Aug. 9, 2013. https://www.pdx.edu/reu/sites/www.pdx.edu.reu/files/Cris%20present.pptx. PowerPoint Presentation. (Year: 2013).*

(Continued)

*Primary Examiner* — Benjamin L Lebron
(74) *Attorney, Agent, or Firm* — Klarquist Sparkman, LLP

(57) ABSTRACT

Embodiments of templated polymeric materials capable of binding lysophosphatidic acids (LPAs) are disclosed. Methods of making and using the templated polymeric materials also are disclosed. The disclosed templated polymeric materials are molecularly imprinted polymers that bind LPAs and facilitate the production of lysophosphatidic acid-enriched samples, for instance through extraction of lysophosphatidic acids from biological samples, such as plasma or serum samples.

22 Claims, 11 Drawing Sheets

(51) Int. Cl.
| | |
|---|---|
| *B01J 20/26* | (2006.01) |
| *B01J 20/281* | (2006.01) |
| *B01J 20/285* | (2006.01) |
| *B01J 20/30* | (2006.01) |
| *C08F 2/44* | (2006.01) |
| *C08F 22/22* | (2006.01) |
| *C12Q 1/02* | (2006.01) |
| *G01N 1/40* | (2006.01) |
| *G01N 33/545* | (2006.01) |
| *G01N 33/92* | (2006.01) |
| *G01N 30/00* | (2006.01) |
| *G01N 30/06* | (2006.01) |

(52) U.S. Cl.
CPC ......... *B01J 20/285* (2013.01); *B01J 20/3057* (2013.01); *C08F 2/44* (2013.01); *C08F 22/22* (2013.01); *C12Q 1/02* (2013.01); *G01N 1/405* (2013.01); *G01N 33/545* (2013.01); *G01N 33/92* (2013.01); *B01J 2220/4812* (2013.01); *B01J 2220/54* (2013.01); *B01J 2220/62* (2013.01); *G01N 2030/009* (2013.01); *G01N 2030/062* (2013.01); *G01N 2405/04* (2013.01); *G01N 2600/00* (2013.01)

(58) Field of Classification Search
CPC . B01J 2220/54; B01J 2220/62; B01D 15/325; B01D 15/426; C08F 2/44; C08F 222/22; C12Q 1/02; G01N 1/405; G01N 33/545; G01N 33/92; G01N 2030/009; G01N 2030/062; G01N 2405/04; G01N 2600/00
See application file for complete search history.

(56) References Cited

OTHER PUBLICATIONS

Sellergren, B., and Andrew Hall. "Molecularly Imprinted Polymers", Supramolecular chemistry: from molecules to nanomaterials. John Wiley & Sons, Ltd. (Year: 2012).*
Extended European Search Report dated Sep. 26, 2018, issued in corresponding European Application No. 16756161.2, 13 pages.
Alptürk, et al. "Lanthanide complexes as fluorescent indicators for neutral sugars and cancer biomarkers." *Proceedings of the National Academy of Sciences* 103, No. 26 (2006): 9756-9760.
Kugimiya, et al. "Selectivity and recovery performance of phosphate-selective molecularly imprinted polymer." *Analytica Chimica Acta* 606, No. 2 (2008): 252-256.
Ochoa, Cris. "Synthesis of Templated Polymeric Materials for Plasma LPA Enrichment" As accessed Jun. 21, 2016, Retrieved from the Internet at URL: <http://www.reu.pdx.edu/presentations/2013/Cris_Ochoa_2013_REU_Symposium_Presentation.pdf>.
Turiel, et al. "Molecularly imprinted polymers for sample preparation: a review." *Analytica Chimica Acta* 668, No. 2 (2010): 87-99. (Abstract only).
Wang, et al. "Simple enrichment and analysis of plasma lysophosphatidic acids." *Analyst* 138, No. 22 (2013): 6852-6859.
Wu, et al. "Comparison of monofunctional and multifunctional monomers in phosphate binding molecularly imprinted polymers." *Journal of Molecular Recognition* 21, No. 6 (2008): 410-418.

* cited by examiner

FIG. 9A
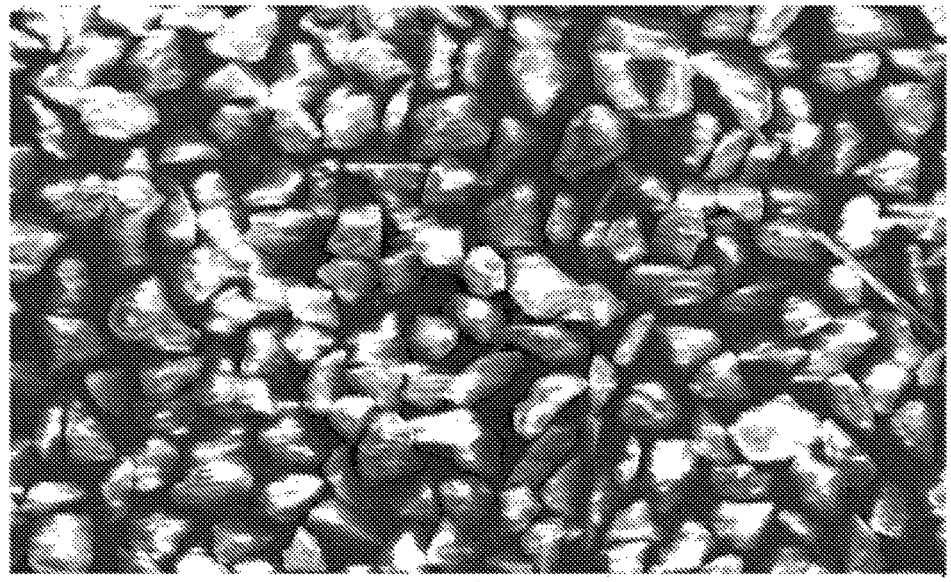
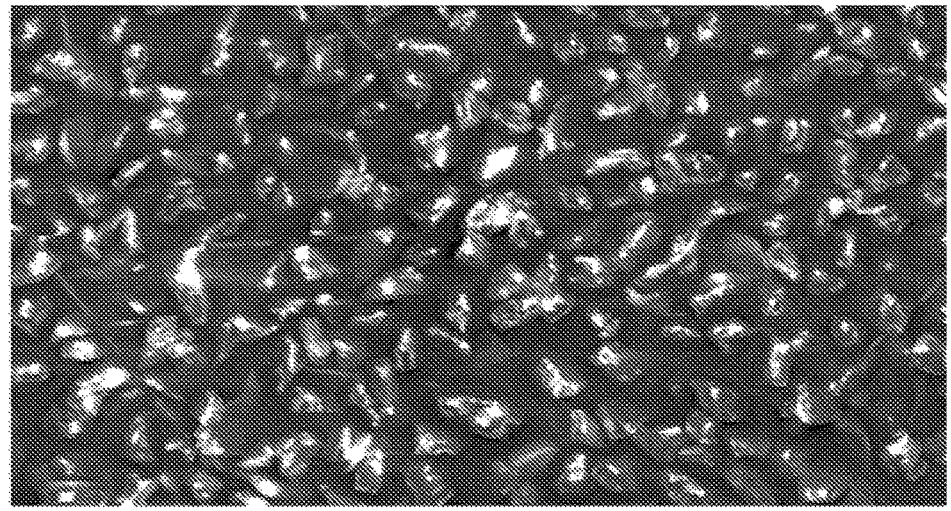
FIG. 9B

ENRICHMENT OF LYSOPHOSPHATIDIC ACIDS WITH TEMPLATED POLYMERIC MATERIALS

CROSS REFERENCE TO RELATED APPLICATIONS

This is the U.S. National Stage of International Application No. PCT/US2016/019072, filed Feb. 23, 2016, which was published in English under PCT Article 21(2), which in turn claims the benefit of U.S. Provisional Application No. 62/126,208, filed Feb. 27, 2015. The provisional application is incorporated by reference in its entirety herein.

ACKNOWLEDGMENT OF GOVERNMENT SUPPORT

This invention was made with government support under Grant No. R01EB002044 awarded by the National Institutes of Health. The government has certain rights in the invention.

FIELD

This disclosure concerns embodiments of templated polymeric materials capable of binding lysophosphatidic acids, and methods of making and using the templated polymeric materials. Kits including the templated polymeric materials also are disclosed.

BACKGROUND

Lysophosphatidic acids (LPAs) are bioactive phospholipids that stimulate cell proliferation, migration, platelet aggregation, and survival. LPAs influence many physiological processes, such as brain and vascular development. Aberrant LPA production, expression, and signalling have been linked to cancer initiation (e.g., tumorigenesis), progression, angiogenesis, and metastasis. LPAs are thought to play a role in a number of cancers, including ovarian cancer, breast cancer, prostate cancer, colorectal cancer, hepatocellular carcinoma, and multiple myeloma. LPAs also have been linked to cardiovascular disease (e.g., atherosclerosis, atherothrombosis), platelet aggregation, pulmonary inflammatory diseases, renal diseases, ischemia perfusion injury, wound healing, neuropathic pain, neuropsychiatric disorders, reproductive disorders, and fibrosis.

Liquid chromatography-mass spectrometry (LC-MS) is one of the most popular quantification methods for LPA, especially for individual LPA quantifications. A wide variety of methods for LPA sample preparation have been developed. Liquid-liquid extraction (LLE) is the common methodology for LPA enrichment for biological samples. For example, the LLE method developed by Bligh-Dyer (Can. J. of Biochemistry and Physiology, 1959, 37, 911-917) has been modified and used in many LPA studies. These modified methods that require one- or two-step extractions are easy and fast. However, they are also problematic, because abundant potential interferences, such as lysophosphatidylcholine (LPC), can be co-extracted with LPA and affect LPA quantifications.

For example, Zhao et al. (J. Chromatography B, 2009, 877:3739-3742) reported that lysophosphatidylcholine (LPC) and lysophosphatidylserine (LPS) could lose the choline or serine head group to artificially generate LPA-like signals in electrospray ionization tandem mass spectrometry (ESI-MS/MS) at the ion source. This fact may greatly affect LPA quantification since the biological concentration of LPC is about 300 µM, which is hundreds of times higher than LPA (less than 5 µM) in healthy people. Meanwhile, some phospholipids, such as glycerophosphocholines and lysophosphatidylcholines, may cause a matrix effect that suppresses or enhances ionization process, shifts the retention time, and/or elevates the baseline. These influences may greatly reduce the accuracy and reproducibility of LPA quantification by LC-MS.

Other quantification methods besides LC-MS may also be affected by the presence of interfering phospholipids in LPA samples because of the similarities between LPA and other phospholipids. For example, phosphatidic acid (PA) has the same head group as LPA; lysophosphatidylethanolamine (LPE), LPS, and LPC all have alkyl chains with the same or similar length as LPA. Thus, if the detection is based on phosphate group binding or deaggregation by the LPA alkyl chain, the phospholipids that co-extracted with LPA from plasma would interfere with the detection and lead to a false positive result. Thus, removal of interferences is critical for an accurate quantification of LPA.

SUMMARY

This disclosure concerns embodiments of molecularly imprinted polymers (MIPs) capable of binding lysophosphatidic acids (LPAs), as well as methods of making and using the templated polymeric materials. Embodiments of the disclosed MIPs comprise a plurality of first structural units derived from monomers comprising (a) at least one functional moiety capable of binding to a phosphate group and (b) at least one polymerizable moiety, the molecularly imprinted polymer having a molecular imprint suitable for binding a lysophosphatidic acid. The MIP is obtained by polymerizing the monomers in a solution comprising (i) a solvent, (ii) a guest molecule comprising an anionic head group and a hydrophobic tail portion, (iii) a crosslinker, and (iv) a radical polymerization initiator (e.g., 2,2'-azobisisobutyronitrile) to produce a polymer containing the guest molecule, and removing the guest molecule from the polymer containing the guest molecule to produce the MIP. In some embodiments, the functional moiety capable of binding to a phosphate group is an amino, —N(H)—C(O)—N(H)—, —N(H)—C(S)—N(H)—, pyridyl, imidazolyl, pyrimidinyl, pyrazinyl, or cyclenyl moiety, or any combination thereof. At least some of the monomers may comprise a plurality of functional moieties capable of binding to a phosphate group. In some embodiments, the polymerizable moiety comprises a terminal ethenyl group.

The first structural units may be derived from monomers according to one of the following five chemical structures or a combination of two or more thereof:

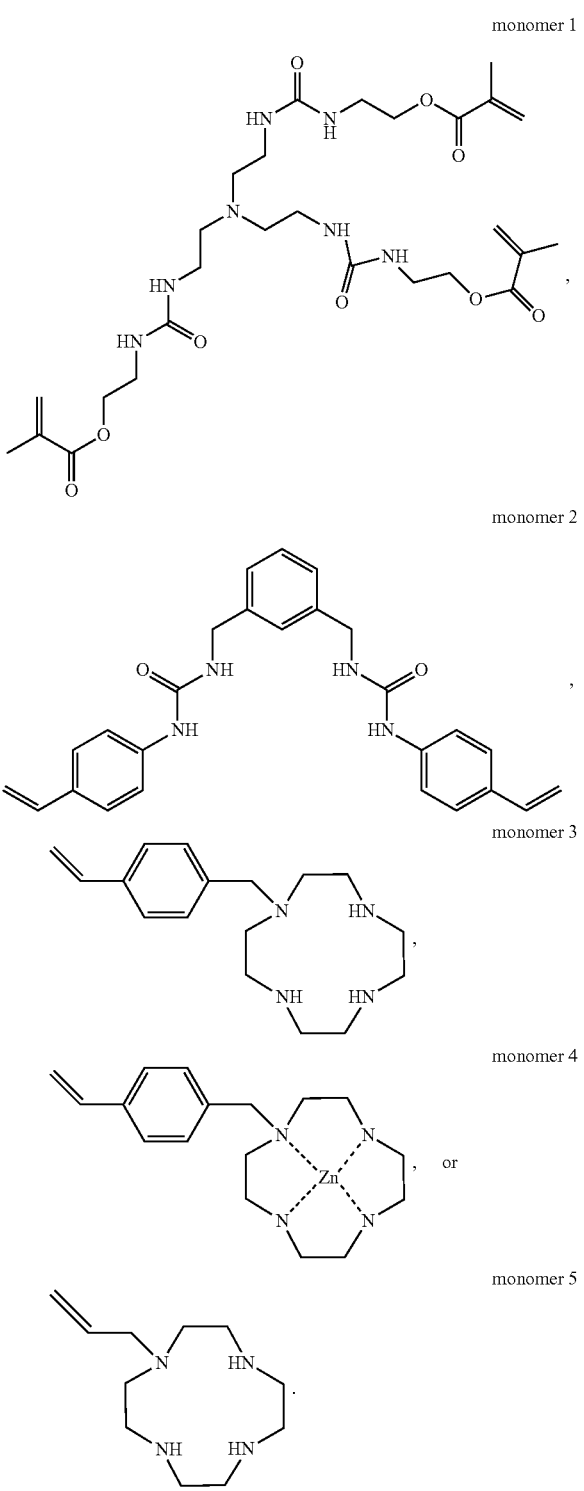

monomer 1 monomer 2 monomer 3 monomer 4 monomer 5

Embodiments of the disclosed MIPs may further comprise a plurality of second structural units derived from monomers capable of binding to at least one of a phosphate acid group or a hydroxyl group. In some embodiments, the second structural units are derived from 2-vinylpyridine, 4-vinylpyridine, 1-vinylimidazole, 4-vinylimidazole, 1-allylthiourea, methacrylic acid, or a combination of two or more thereof.

In some embodiments, the guest molecule comprises an anionic head comprising a phosphate or phosphonic acid group. The guest molecule may comprise a hydrophobic tail comprising a single aliphatic or heteroaliphatic chain. In certain embodiments, the guest molecule is octadecylphosphonic acid.

Suitable crosslinkers include ethylene glycol dimethacrylate (EGDMA), divinylbenzene (DVB), tetraethylene glycol dimethacrylate (TEGDMA), N,O-bismethacrylolyl ethanolamine (NOBE), N,N'-methylenebismethacrylamide (MMAA), triallyl isocyanurate (TAIL), trimethylolpropane trimethacrylate (TRIM), or a combination of two or more thereof. The crosslinker may be present in molar excess. In some embodiments, the MIP comprises first structural units derived from monomer 1 and the crosslinker in a mole ratio of 1:5 to 1:50. In certain embodiments, the MIP comprises first structural units derived from monomer 1, second structural units derived from methacrylic acid, and EGDMA in a 1:1:20 mole ratio.

Embodiments of the disclosed method for making a MIP for binding a lysophosphatidic acid include polymerizing monomers comprising (a) at least one functional moiety capable of binding to a phosphate group and (b) at least one polymerizable moiety in a solution comprising (i) a solvent, (ii) a guest molecule comprising an anionic head group and a hydrophobic tail portion, (iii) a crosslinker, and (iv) a radical polymerization initiator to produce a polymer containing the anionic guest molecule; and removing the guest molecule from the polymer containing the guest molecule to produce a molecularly imprinted polymer having a molecular imprint capable of binding lysophosphatidic acid. The guest molecule may be removed by extraction with a lower alkyl alcohol, such as by Soxhlet extraction with methanol.

Embodiments of a method of preparing a lysophosphatidic acid-enriched sample include (i) loading a solution comprising one or more lysophosphatidic acid species onto a solid-phase extraction cartridge including a stationary phase comprising an embodiment of the disclosed MIPs (MIP SPE cartridge); (ii) flowing chloroform and subsequently a lower alkyl alcohol (e.g., methanol) through the MIP SPE cartridge; and (iii) flowing an alkaline solution comprising a lower alkyl alcohol (e.g., 0.05 wt % NH$_4$OH in methanol) through the MIP SPE cartridge, thereby eluting at least a portion of the lysophosphatidic acid species from the MIP SPE cartridge to provide a lysophosphatidic acid-enriched sample.

In some embodiments, the solution comprising one or more LPA species is prepared by (i) combining a sample comprising plasma or serum with a solvent comprising a lower alkyl alcohol and chloroform to form a mixture; (ii) separating the mixture to provide a supernatant and a precipitate; and (iii) acidifying the supernatant to provide the solution comprising one or more lysophosphatidic acid species. The supernatant may be acidified, such as with formic acid, to a pH within a range of 1-5. In certain embodiments, one part of the plasma or serum sample is combined with 3-5 parts of a solvent comprising methanol and chloroform in a ratio of 2:1. The mixture may be incubated at 4° C. for a period of time and then warmed to ambient temperature before separating the mixture.

In some embodiments, after the mixture is separated, the supernatant is loaded onto a SPE cartridge including a stationary phase comprising a non-imprinted polymer (NIP) comprising (i) a plurality of first structural units derived from monomers comprising (a) at least one functional moiety capable of binding to a phosphate group and (b) at least one polymerizable moiety (NIP SPE cartridge), and (ii)

a crosslinker. An alkaline solution comprising a lower alkyl alcohol is flowed through the NIP SPE cartridge to provide an eluent, which is acidified to provide the solution comprising one or more LPAs. The solution is then loaded onto a MIP SPE cartridge as described above. The NIP and MIP may have the same or different chemical compositions.

The lysophosphatidic acid-enriched sample may be dried by evaporating solvent to form a dry residue comprising the LPA species. The residue may be dissolved in a solvent for further analysis. Further analysis may include (i) determining a total concentration of LPA species in the sample comprising plasma or serum, and/or (ii) separating LPA species in the lysophosphatidic acid-enriched sample using a reversed-phase high-performance liquid chromatography (HPLC) column, and detecting individual LPA species as or after the separated LPA species exit the reversed-phase HPLC column. The concentration of individual LPA species in a sample comprising plasma or serum may be determined.

This disclosure includes embodiments of kits comprising at least one MIP as disclosed herein. The MIP may be disposed within a SPE cartridge. In some embodiments, the kit further includes a NIP, which may be disposed in a second SPE cartridge. The NIP and MIP may have the same or different chemical compositions.

The foregoing and other objects, features, and advantages will become more apparent from the following detailed description, which proceeds with reference to the accompanying figures.

BRIEF DESCRIPTION OF THE DRAWINGS

FIGS. 9A and 9B are SEM microphotographs of a ground non-imprinted polymer (FIG. 9A) and a molecularly imprinted polymer (FIG. 9B) made according to an embodiment of the disclosed method.

DETAILED DESCRIPTION

Figure 1:
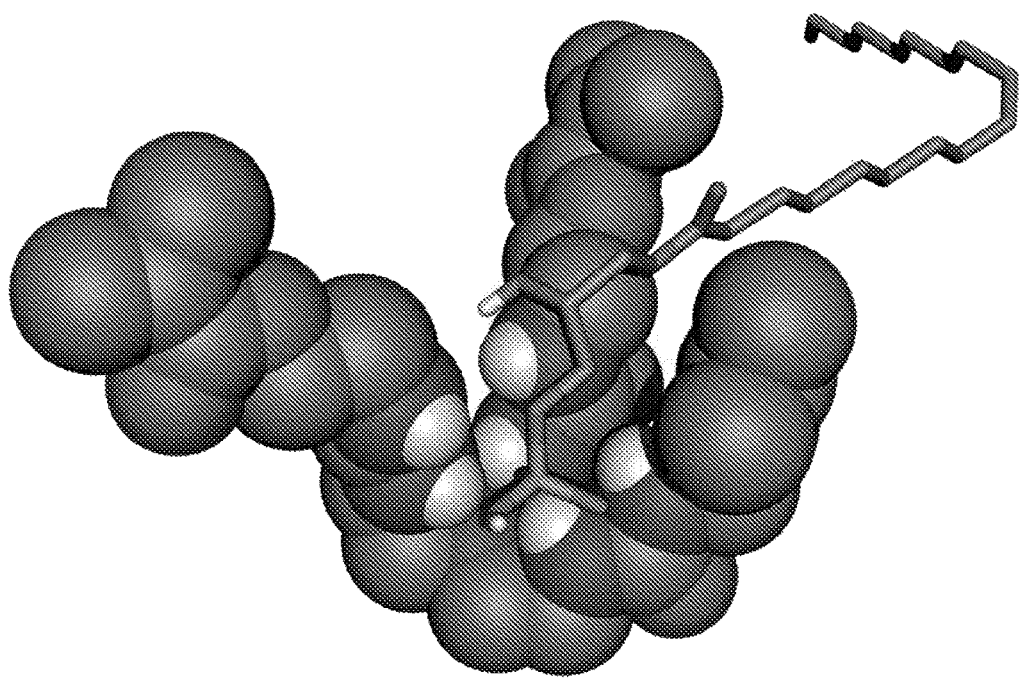
FIG. 1 is an energy-minimized structure of a complex formed with monomer 1 and lysophosphatidic acid 18:1.

Embodiments of templated polymeric materials capable of binding lysophosphatidic acids (LPAs) are disclosed. Methods of making and using the templated polymeric materials also are disclosed. The disclosed templated polymeric materials are molecularly imprinted polymers that bind LPAs and facilitate formation of lysophosphatidic acid-enriched samples through extraction of lysophosphatidic acids from biological samples, such as plasma or serum samples. Advantageously, the disclosed molecularly imprinted polymers (MIPs) provide a means for solid-phase extraction of LPAs in contrast to known methods that require multiple liquid-liquid extractions. The MIPs are suitable for use in cartridges, e.g., solid-phase extraction cartridges. Some embodiments of the disclosed MIPs readily separate the five major species of lysophosphatidic acid from other native plasma phospholipids, including those well-known to interfere with LPA quantitation, such as phosphatidyl choline and lysophosphatidylcholine.

I. TERMS AND ABBREVIATIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, solvent ratios, e.g., methanol and chloroform 2:1, are ratios by volume.

Unless otherwise indicated, all numbers expressing quantities of ingredients, properties such as molecular weight, percentages, and so forth, as used in the specification or claims are to be understood as being modified by the term "about." Accordingly, unless otherwise indicated, implicitly or explicitly, the numerical parameters set forth are approximations that may depend on the desired properties sought, limits of detection under standard test conditions/methods, limitations of the processing method, and/or the nature of the parameter or property. When directly and explicitly distinguishing embodiments from discussed prior art, the embodiment numbers are not approximates unless the word "about" is recited.

Aliphatic: A substantially hydrocarbon-based compound, or a radical thereof (e.g., $C_6H_{13}$, for a hexane radical), including alkanes, alkenes, alkynes, including straight- and branched-chain arrangements, and all stereo and position isomers as well. Unless expressly stated otherwise, an aliphatic group contains from one to twenty-five carbon atoms. An aliphatic chain may be substituted or unsubstituted. Unless expressly referred to as an "unsubstituted aliphatic," an aliphatic group can either be unsubstituted or substituted. An aliphatic group can be substituted with one or more substituents (up to two substituents for each methylene carbon in an aliphatic chain, or up to one substituent for each carbon of a —C═C— double bond in an aliphatic chain, or up to one substituent for a carbon of a terminal methine group). Exemplary substituents include, but are not limited to, alkyl, alkenyl, alkynyl, alkoxy, carbonyl, carboxyl, halo, haloaliphatic, heteroaliphatic, hydroxyl, oxo, sulfhydryl, or other functionality.

Alkyl: A hydrocarbon group having a saturated carbon chain. The chain may be cyclic, branched or unbranched. The term lower alkyl means the chain includes 1-10 carbon atoms.

Allyl: A hydrocarbon group with the structural formula $H_2C$═CH—$CH_2$—.

Amino: A chemical functional group —N(R)R' where R and R' are independently hydrogen, alkyl, heteroalkyl, haloalkyl, aliphatic, heteroaliphatic, aryl (such as optionally substituted phenyl or benzyl), heteroaryl, alkylsulfano, or other functionality. A "primary amino" group is —$NH_2$. "Mono-substituted amino" or "secondary amino" means a radical —N(H)R substituted as above and includes, e.g., methylamino, (1-methylethyl)amino, phenylamino, and the like. "Di-substituted amino" (or tertiary amino) means a radical —N(R)R' substituted as above wherein R and R' are other than hydrogen and includes, e.g., dimethylamino, methylethylamino, di(1-methylethyl)amino, and the like.

Carboxyl: A —COOH radical.

Cyclen: 1,4,7,10-tetrazocyclodecane, a macrocyclic aza analog of the crown ether 12-crown-4:

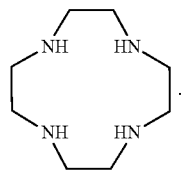 [SMILES: C1CNCCNCCNCCN1]

As used herein, the term "cyclen" also encompasses cyclen derivatives, such as cyclen salts having a central metal cation (e.g., $Zn^{2+}$) and larger cyclic polyamines having repeating ethyleneimine units. A cyclenyl group is a cyclen with a free valence on one of the nitrogen atoms.

Functional group or moiety: A specific group of atoms within a molecule that is responsible for the characteristic chemical reactions of the molecule. Exemplary functional groups include, without limitation, alkyl, alkenyl, alkynyl, aryl, halo (fluoro, chloro, bromo, iodo), epoxide, hydroxyl, carbonyl (ketone), aldehyde, carbonate ester, carboxylate, carboxyl, ether, ester, peroxy, hydroperoxy, carboxamide, amino (primary, secondary, tertiary), ammonium, imide, azide, cyanate, isocyanate, thiocyanate, nitrate, nitrite, nitrile, nitroalkyl, nitroso, pyridyl, imidazolyl, pyrimidinyl, pyrazinyl, phosphate, sulfonyl, sulfide, thiol (sulfhydryl), disulfide, urea (—N(H)—C(O)—N(H)—), thiourea (—N(H)—C(S)—N(H)—).

Functional monomer: As used herein, the term "functional monomer" refers to a monomer comprising at least one functional moiety capable of binding non-covalently (e.g., via hydrogen bonding and/or electrostatic interactions) to a functional group, e.g., a phosphate group and/or a hydroxyl group, of a lysophosphatidic acid.

Guest molecule or template molecule: A molecule used as a template in the preparation of a molecularly imprinted polymer. The guest molecule is subsequently removed, leaving a molecular imprint in the polymer.

Heteroaliphatic: An aliphatic compound or group having at least one heteroatom, i.e., one or more carbon atoms has been replaced with an atom having at least one lone pair of electrons, typically nitrogen, oxygen, phosphorus, silicon, or sulfur. Heteroaliphatic compounds or groups may be substituted or unsubstituted, branched or unbranched.

Initiator: An agent used to start polymerization of a monomer. The initiator typically is consumed in the reaction. In polymerization, the initiator typically forms a free radical to initiate the reaction. Such initiators may be referred to as radical polymerization initiators. Initiators include, by way of example and without limitation, halogens, azo compounds (R—N═N—R', where R and R' denote aliphatic, alkyl, and/or aryl groups, or combinations thereof), and organic peroxides (R—O—O—R', R and R' denote aliphatic, alkyl, and/or aryl groups, or combinations thereof).

LPA: lysophosphatidic acid

LPS: lysophosphatidylserine

Lysophosphatidic acid (LPA): A family of phospholipid derivatives. Lysophosphatidic acid is found in both eukaryotic and prokaryotic cells, including in plant and animal cells. The following five major species are found in humans (though LPA 17:0, although listed, is not a naturally occurring LPA):

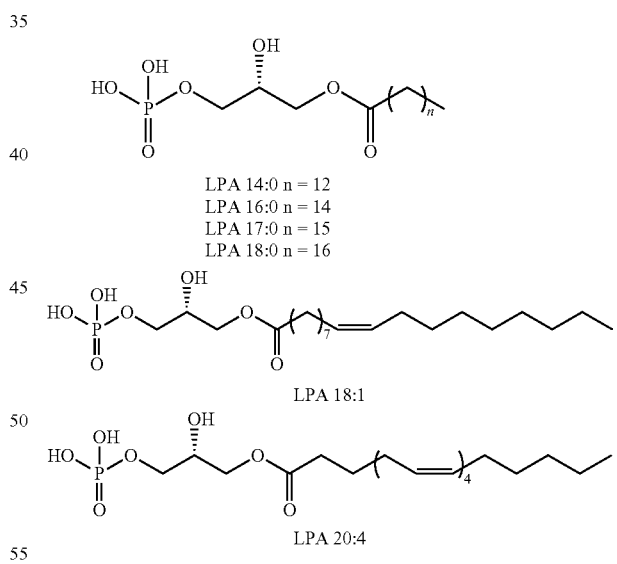

MIP: molecularly imprinted polymer

Molecularly imprinted polymer (MIP): A crosslinked polymer synthesized from monomers and a template or guest molecule, followed by removal of the guest molecule, leaving a polymer having imprints or cavities corresponding to the shape of the guest molecule. The imprints or cavities have an affinity for the guest molecule or other molecules with similar shape and/or functional group(s).

Monomer: A molecule or compound, usually containing carbon, that can react and combine to form polymers. Common monomers include, for example and without limitation, alkenes, amides, arenes), and unsaturated carboxylic acids (e.g., acrylic acid, methacrylic acid, among others).

NIP: non-imprinted polymer

Octadecylphosphonic acid: $CH_3(CH_2)_{17}P(O)(OH)_2$

PA: phosphatidic acid

PC: phosphatidyl choline

PE: phosphatidyl ethanolamine

Polymer: A molecule of repeating structural units (derived from monomers) formed via a chemical reaction, i.e., polymerization.

SPE: solid phase extraction

Structural unit: As used herein, the term "structural unit" refers to a unit of a polymer derived from polymerization of monomers. For example, a polymer of methacrylic acid includes structural units derived from methacrylic acid monomers and having the formula shown within brackets:

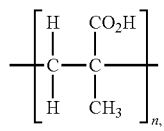

Surfactant: A compound that reduces surface tension when dissolved in water or water solutions, or that reduces interfacial tension between two liquids. A surfactant molecule typically has a polar or ionic "head" and a nonpolar hydrocarbon "tail." An anionic surfactant comprises an anionic group at the head, e.g., a sulfate, sulfonate, phosphate, or carboxylate group.

Vinyl: A hydrocarbon group with the structural formula $H_2C=CH-$.

II. MOLECULARLY IMPRINTED POLYMERS AND METHODS OF MAKING

Molecularly imprinted polymers (MIPs) are highly crosslinked polymers that can be used as artificial receptors for specific molecules. MIPs are synthesized by covalently or noncovalently binding a template, or guest, molecule and functional monomers, followed by polymerization. Typically, copolymerization with a high concentration of crosslinking monomers is performed. The guest molecule is then removed, leaving a polymer with complementary cavities and binding sites (i.e., molecular imprints) that can be used to selectively bind target molecules. The result is similar to the "lock and key" model of an enzyme and substrate. MIPs can be customized and modified by varying the selection and composition of the functional monomers and crosslinking monomers. In the disclosed embodiments, the MIP has a molecular imprint that suitable for binding a lysophosphatidic acid. By "suitable for" is meant that the molecular imprint has a size and shape complementary to lysophosphatidic acid.

In the disclosed embodiments, a functional monomer for making a MIP capable of binding lysophosphatidic acids comprises at least one functional moiety capable of binding to a phosphate group and at least one polymerizable moiety (e.g., a terminal ethenyl group). Functional monomers may be commercially available, or may be synthesized to provide functionalities suitable for target compounds and increase selectivity. In some embodiments, each functional monomer may comprise multiple functional moieties, thereby increasing binding affinity to the template molecule during synthesis and reducing subsequent nonspecific binding to non-targeted molecules.

Functional monomers for producing a MIP capable of binding lysophosphatidic acids include one or more functional moieties that can bind to a phosphate group via hydrogen bonding and electrostatic interactions. For example, the N—H groups in urea can bind to a phosphate group via hydrogen bonding and electrostatic interactions. Exemplary functional moieties include, but are not limited to amino (e.g., primary or secondary amino), —N(H)—C(O)—N(H)—, —N(H)—C(S)—N(H)—, pyridyl, imidazolyl, pyrimidinyl, pyrazinyl, and cyclenyl moieties, as well as combinations thereof. In some embodiments, a functional monomer comprises at least two functional moieties; the moieties may be the same or different from one another. When multiple functional groups are present, at least one of the functional groups may be capable of binding to a hydroxyl group.

Embodiments of the disclosed MIPs comprise a plurality of structural units derived from monomers comprising (a) at least one functional moiety capable of binding to a phosphate group and (b) at least one polymerizable moiety, the MIP having a molecular imprint suitable for binding a lysophosphatidic acid. In certain embodiments, the MIP comprises a plurality of structural units derived from monomers according to one of the following five chemical structures or a combination of two or more thereof:

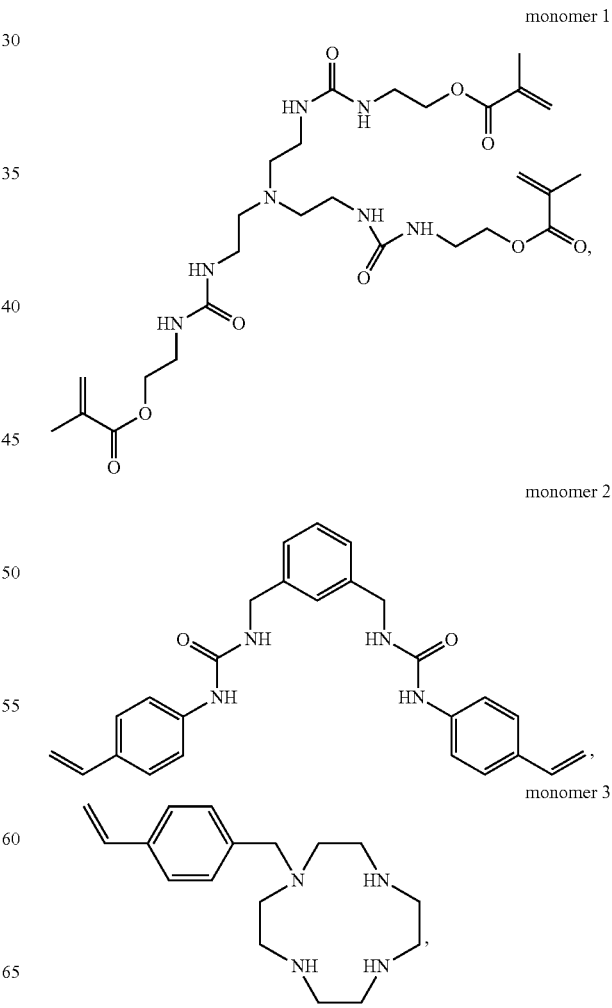

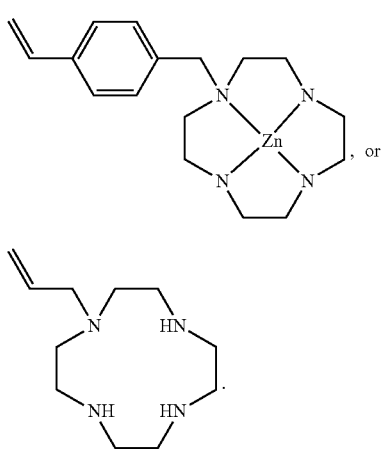

monomer 4 monomer 5

Monomers 1 and 2 include three or two urea (—N(H)—C(O)—N(H)—) moieties, respectively. Monomers 3-5 each include a cyclenyl moiety.

FIG. 1 is an energy minimized, space-fill model of a 1:1 complex of monomer 1 and lysophosphatidic acid 18:1 using the SYBYL-X™ 20 Suite (Certara, L. P., Princeton, N.J.). Atom colors: carbon=gray, hydrogen=white, oxygen=red, nitrogen=blue, phosphorus=orange. For clarity, only polar hydrogens are shown.

Figure 2:
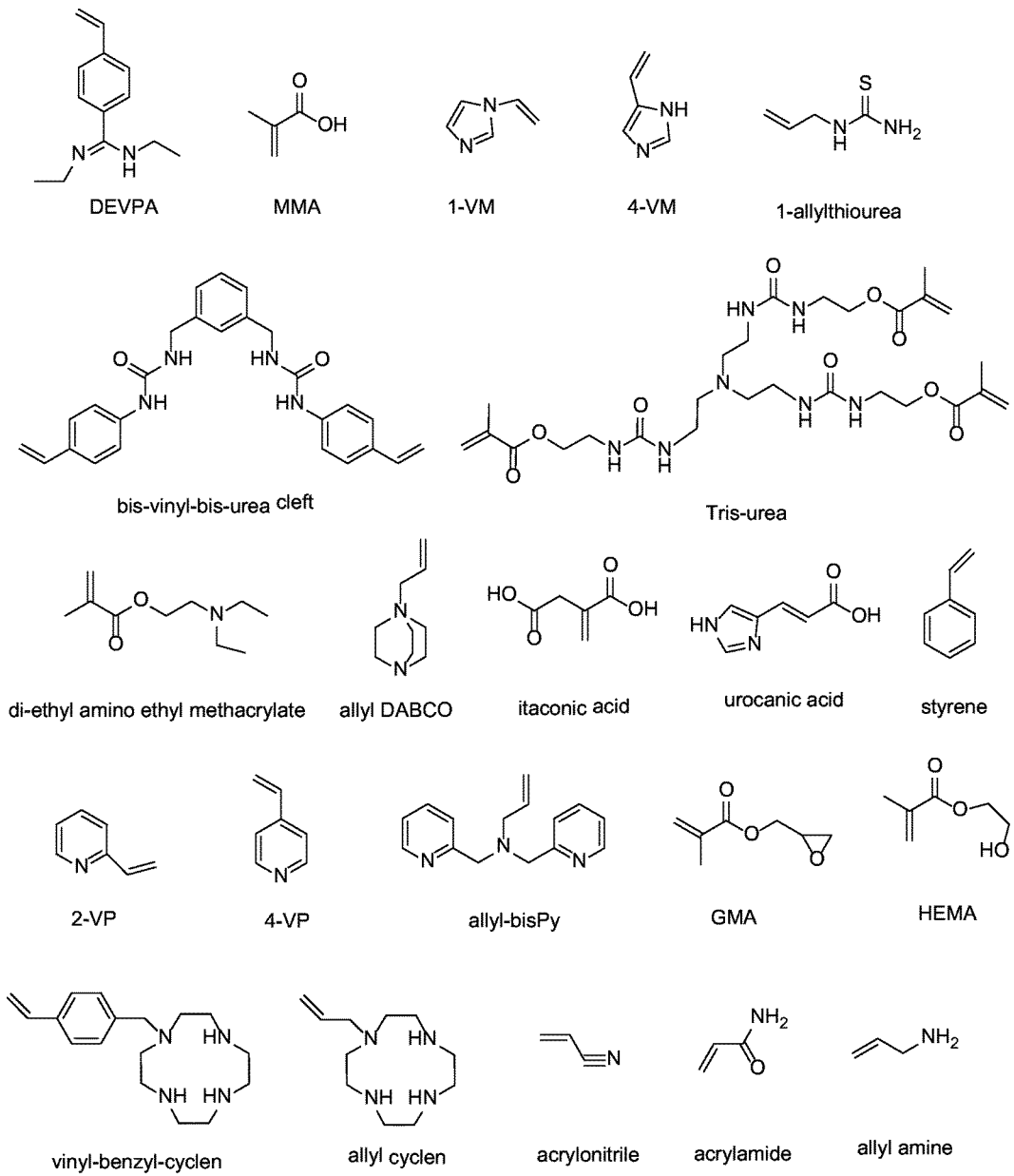
FIG. 2 shows chemical structures of 22 functional monomers selected from a virtual library.

A molecularly imprinted polymer may include structural units derived from a single functional monomer. In some embodiments, the MIP has structural units derived from two or more functional monomers, e.g., first structural units derived from a first functional monomer and second structural units derived from a second functional monomer. A second functional monomer may have a functional moiety capable of binding to the phosphate group of lysophosphatidic acid and/or to the hydroxyl group of LPA. Exemplary functional moieties capable of binding to the hydroxyl group include, but are not limited to, carboxyl, imidazole, pyridine, pyrimidine, pyrazine, thiourea, and urea groups. In some embodiments, the second functional monomer is 2-vinylpyridine, 4-vinylpyridine, 1-vinylimidazole, 4-vinylimidazole, 1-allylthiourea, methacrylic acid, or a combination of two or more thereof. Additional functional monomers are shown in FIG. 2. An MIP may include structural units derived from two monomers in a mole ratio from 10:1 to 1:10, such as a ratio from 5:1 to 1:5 or from 2:1 to 1:2. In some embodiments, the MIP is synthesized from a first functional monomer and a second functional monomer in a mole ratio of 1:1.

The presence of a second monomer may increase recovery of lysophosphatidic acids. In some examples, a MIP made from a single functional monomer had LPA recoveries of 60-80%, whereas an MIP made from two different functional monomers had LPA recoveries of at least 70%, such as from 70-100%. Addition of a second monomer may also increase specificity for LPA. In certain examples, an MIP synthesized from monomer 1 bound LPAs well, but also bound 70-80% of phosphatidic acid in a sample. In contrast, an MIP synthesized from monomer 1 and methacrylic acid increased recovery of LPAs while reducing PA recovery by half because PA does not have a hydroxyl group capable of binding to the carboxyl group.

The molecular imprint is provided by synthesizing the polymer in the presence of a template or guest molecule and crosslinking monomers. The guest molecule may be the desired target molecule (e.g., a LPA) or a molecule with similar structure and functionality. A disadvantage to using the target molecule as the guest molecule is that incomplete removal of the guest molecule after polymerization potentially interferes with detection and/or quantification, resulting in false positives and/or artificially high recoveries of LPA from samples. Thus, in some embodiments, the guest molecule is a molecule with similar structure and functionality as LPA or a molecule that corresponds to a structural fragment of LPA (e.g., a phosphonic acid or glycerol phosphate). The guest molecule desirably has an anionic "head" and a hydrophobic, typically aliphatic or heteroaliphatic, "tail." In some embodiments, the anionic head is a phosphate or phosphonic acid group. The guest molecule may have a tail similar in length to LPAs, e.g., a tail having a length from 12-24 carbons, such as a length from 14-20 carbons. Suitable guest molecules may include phosphate monoesters. Desirably, the guest molecule has a tail that is a single aliphatic or heteroaliphatic chain, such as a hydrocarbon chain, thereby decreasing affinity of the resulting imprint for PA, which has a double-chain tail. An exemplary guest molecule is octadecylphosphonic acid.

Embodiments of the disclosed MIPs are crosslinked polymers. In some embodiments, the MIPs are highly crosslinked. By "highly crosslinked" is meant that the polymer is prepared with a molar excess of crosslinking monomers compared to the functional monomers. Crosslinking monomers are combined with complexes comprising the functional monomer(s) and the guest molecules, and then polymerized. The crosslinking monomers form a three-dimensional network around the complex and "lock" the functional monomer(s) in place with the configuration attained during complex formation. In some embodiments, the MIP is synthesized from one or more functional monomers and one or more crosslinking monomers in a mole ratio of 1:2 to 1:50, such as a ratio from 1:4 to 1:30. In certain embodiments, the mole ratio of functional monomer to crosslinking monomer is 1:20. Suitable crosslinking monomers include, but are not limited to, ethylene glycol dimethacrylate (EGDMA), divinylbenzene (DVB), tetraethylene glycol dimethacrylate (TEGDMA), N,O-bismethacrylolyl ethanolamine (NOBE), N,N'-methylene-bismethacrylamide (MMAA), triallyl isocyanurate (TAIL), trimethylolpropane trimethacrylate (TRIM), and combinations thereof (see, e.g., FIG. 3).

Embodiments of the disclosed MIPs are synthesized by polymerizing functional monomers comprising (a) at least one functional moiety capable of binding to a phosphate group and (b) at least one polymerizable moiety in a solution comprising (i) a solvent, (ii) a guest molecule comprising an anionic head group and a hydrophobic tail portion, (iii) a crosslinker, and (iv) a radical polymerization initiator. In some embodiments, the functional monomers and guest molecule are present in a mole ratio from 5:1 to 1:5, such as from 3:1 to 1:3, 2:1 to 1:2, or 1.5:1 to 1:1.5. In exemplary embodiments, the functional monomers and guest molecule were present in a mole ratio of 1:1. A second functional monomer may be included in the synthesis. When a second functional monomer is present, the molar ratios of the first and second functional monomers may be selected to provide optimal binding of the analyte, i.e., lysophosphatidic acid. In certain embodiments, a first functional monomer, second functional monomer, and guest molecule were present in a 1:1:1 mole ratio.

In some embodiments, the guest molecules and functional monomers are combined in a solvent for a period of time before initiating polymerization, thereby allowing complexes between the guest molecules and functional monomers to form before polymerization occurs. The guest molecule may bind covalently or non-covalently (e.g., hydrogen bonding, van der Waals' forces) to the functional monomers. A solvent in which both the guest molecule and the functional monomers are soluble is selected. Suitable solvents include nonpolar and relatively nonpolar solvents (e.g., acetonitrile, chloroform, toluene, methylene chloride) and non-protic polar solvents (e.g., dimethylsulfoxide, dimethylformamide). Polar protic solvents are not suitable. In some embodiments, the solvent is chloroform. The period of time may be from several minutes to several hours, such as from 15 minutes to 2 hours or from 30-90 minutes.

After complex formation has occurred, the crosslinking monomers and polymerization initiator are added, and polymerization proceeds at an effective temperature for an effective period of time. Suitable polymerization initiators include radical polymerization initiators. Radical polymerization initiators include, but are not limited to, azo compounds, inorganic peroxides, and organic peroxides. In some examples, the initiator was 2,2'-azobisisobutyronitrile (AIBN). The effective period of time may be from several minutes to several hours, such as from 2-48 hours, 6-24 hours, or 12-20 hours. The effective temperature may depend at least in part on the selection of the monomers, crosslinking monomer, polymerization initiator, and solvent. In some embodiments, the effective temperature is from ambient temperature to near boiling, such as from 30-70° C. When the solvent was chloroform and the monomers included monomer 1, polymerization was carried out from 50-60° C.

Following polymerization, the polymer is optionally crushed and then washed, e.g., with a lower alkyl alcohol such as methanol. The template or guest molecule is then removed. The guest molecule may be removed by extraction, such as by Soxhlet extraction. Extraction also removes residual monomers, oligomers, and initiator molecules. Extraction is performed with a solvent capable of dissolving the guest molecule without dissolving the polymer. When octadecylphosphonic acid is the guest molecule, a lower alkyl alcohol (e.g., methanol) is a suitable solvent for extraction. Extraction is performed for an effective period of time to remove a majority of the guest molecule. The effective period of time may be from several hours to several days, such as from 12 hours to 4 days, 1-3 days, or 36 hours to 2 days. In some embodiments, at least 80%, at least 85%, at least 90%, or at least 95% of the guest molecule is removed by extraction.

The resulting MIP may be ground and/or sieved as desired before use. The MIP may be stored dry (e.g., as a dry powder) at ambient temperature before use.

In some embodiments, a non-imprinted polymer (NIP) is synthesized. The NIP can serve as a "control" to evaluate efficacy of the molecularly imprinted polymer. In some embodiments, as described below, the NIP is useful for binding and removing interferences from a sample. The NIP is synthesized by a similar process as the MIP, but in the absence of the guest molecule.

III. METHOD OF EXTRACTING LPA AND PREPARING AN ENRICHED SAMPLE

LPAs are found in plasma and serum. To accurately quantify total LPA and/or to separate, identify, and quantify LPA species, the LPAs must be extracted from the plasma or serum sample and separated from potential interferences, including other phospholipids (e.g., phosphatidic acid, phosphatidyl choline, lysophosphatidylcholine, lysophosphatidylserine, phosphatidyl ethanolamine, phosphatidyl inositol, and sphingosine-1-phosphate) that may interfere.

Conventional methods for extracting LPAs insufficiently remove interferences and/or produce poor LPA recoveries. These methods do not adequately prepare LPA samples for quantifying total LPA, or for HPLC separation and subsequent identification/quantification of individual LPA species.

Embodiments of the disclosed method for LPA extraction comprise contacting a sample comprising, or potentially comprising, LPAs with an embodiment of a molecularly imprinted polymer as disclosed herein. The sample may be a biological sample, such as a plasma or serum sample. The plasma or serum sample typically is combined with a solvent prior to contact with the MIP. In some embodiments, the solvent is a mixture of a lower alkyl alcohol and chloroform. In certain examples, the solvent comprises methanol and chloroform in a ratio of 2:1 by volume. Contacting may be performed by flowing the sample across or through ground MIP. In some examples, a sample prepared from 600 µL was contacted with 30 mg MIP. In some embodiments, the MIP is disposed in a cartridge to provide a solid phase extraction cartridge, and the sample is flowed through the SPE cartridge. The MIP may be preconditioned before use. For example, the MIP may be presoaked for a period of time in a solvent, such as chloroform, to wet and expand the MIP before it is disposed in the SPE cartridge. In some embodiments, the MIP is placed in chloroform for one hour before packing the MIP into the SPE cartridge.

In some embodiments, the sample is acidified before contact with the MIP. The sample may be acidified to a pH of from 1-5, such as a pH from 2 to 4 or from 2.5 to 3.5. In certain examples, the sample was acidified with formic acid. Unbound and/or loosely bound components are removed from the MIP by washing the MIP with one or more solvents. In some embodiments, the MIP is washed with chloroform followed by a lower alkyl alcohol, such as methanol. At least a portion of the LPAs are then eluted from the MIP with an alkaline solution comprising a lower alkyl alcohol, such as 0.05 wt % $NH_4OH$ in methanol to provide a lysophosphatidic acid-enriched sample. In some embodiments, at least 50%, at least 60%, at least 70%, at least 80%, at least 90%, or at least 95% of the LPAs are eluted from the MIP.

The lysophosphatidic acid-enriched sample may be dried, e.g., with a nitrogen stream, to provide a residue comprising LPAs. The dried residue may be resuspended in a solvent suitable for further analysis. In some embodiments, LPAs are dried and resuspended in a methanol-water 9:1 solution for LC-ESI/MS analysis.

Some embodiments of the disclosed method are suitable for LPA extraction from plasma or serum. Such embodiments may include a liquid-liquid extraction followed by the solid phase extraction (SPE) process. Liquid-liquid extraction may be performed with a solvent mixture comprising a lower alkyl alcohol (e.g., methanol, ethanol) and a relatively nonpolar solvent. In some examples, a solvent comprising methanol and chloroform, such as 2:1 $MeOH:CHCl_3$, is mixed with a plasma or serum sample in a ratio of 3-5 parts solvent to one part plasma/serum to form a mixture. The mixture is incubated at 4° C. for a period of time, and then warmed to ambient temperature (e.g., 20° C.). In some embodiments, the effective period of time is at least 15 minutes, such as 15-30 minutes. In certain examples, the effective period of time is 20 minutes. The mixture is separated (e.g., by centrifugation) to provide a supernatant and a precipitate, and the supernatant is recovered. The supernatant is acidified, and the acidified solution is loaded onto the SPE cartridge containing the MIP.

In certain embodiments, the method comprises contacting an LPA-containing solution, such as the separated supernatant, with a non-imprinted polymer (NIP) prior to acidification and contact with the MIP. The NIP removes at least some interfering components, such as interfering phospholipids (e.g., phosphatidic acid, phosphatidyl choline, phosphatidyl serine, phosphatidyl ethanolamine, lysophosphatidylcholine, lysophosphatidylserine, etc.), from the sample prior to contact with the MIP.

The NIP comprises a first structural unit derived from monomers comprising (a) at least one functional moiety capable of binding to a phosphate group and (b) at least one polymerizable moiety. Suitable monomers include those described above for the MIP. The first structural unit may be derived from at least one of monomers 1-5. The NIP typically further includes a crosslinker. Suitable crosslinkers include, but are not limited to, those suitable for the MIP. In some embodiments, the NIP also comprises structural units derived from a second monomer. Suitable second monomers include those described above for the MIP. The NIP is synthesized in the absence of a guest molecule. In some embodiments, the NIP and MIP are synthesized from the same functional monomers, crosslinking monomers, and polymerization initiators with the same molar ratios. Interfering components, such as phosphatidic acid, are more likely than LPAs to bind to the NIP. Because PA has two hydrocarbon chains and does not include the polar hydroxyl group of LPA, it may have more nonspecific interactions with the NIP. Including a hydrophobic monomer, such as divinylbenzene, may increase binding of interfering components such as PA to the NIP.

After contacting the NIP with the aqueous layer, the NIP is washed with an alkaline solution comprising a lower alkyl alcohol to provide an eluent comprising LPAs. In some embodiments, the alkaline solution is 0.05 wt % $NH_4OH$ in methanol. The eluent comprising LPAs is acidified as previously described before being loaded onto the SPE cartridge containing the MIP. This method is referred to as a "tandem" procedure. In the tandem procedure, two SPE cartridges—a first cartridge containing the NIP and a subsequent cartridge containing the MIP—are used in series to further enrich and purify LPAs in a sample, such as a biological sample (e.g., plasma or serum).

In an exemplary embodiment, human plasma is mixed with MeOH—$CHCl_3$ 2:1, and incubated at 4° C. for 15-30 minutes. In some examples, one part plasma is mixed with 3-5 parts MeOH—$CHCl_3$. For example, 600 µL plasma may be mixed with 2 mL MeOH—$CHCl_3$ 2:1. After warming to room temperature, the mixture is centrifuged, and the supernatant is loaded onto a SPE cartridge containing an embodiment of the disclosed NIPs. The SPE cartridge is eluted with an alkaline solution of a lower alkyl alcohol (e.g., 0.05 wt % $NH_4OH$ in methanol) to provide an eluent comprising LPAs. In some embodiments, the NIP-containing SPE cartridge is eluted with 2 mL 0.05 wt % $NH_4OH$ in methanol. The eluent is acidified to pH 2.5-3.5. In some examples, the eluent is acidified with formic acid to pH 3.0. The acidified eluent is loaded onto a SPE cartridge containing an embodiment of the disclosed MIPs. The MIP-containing cartridge is washed with chloroform followed by a lower alkyl alcohol (e.g., methanol). LPAs are eluted with an alkaline solution of a lower alkyl alcohol (e.g., 0.05 wt % $NH_4OH$ in methanol). When the SPE cartridge contains 30 mg of MIP, the MIP-containing SPE cartridge may be washed with 2 mL $CHCl_3$, followed by 2 mL methanol, and then 3 mL 0.05 wt % $NH_4OH$ in methanol to provide eluted LPAs. The solvent may be evaporated, e.g., under a nitrogen stream, and the LPA-containing residue reconstituted in an aqueous methanol solution, e.g., 0.2 mL MeOH—$H_2O$ 9:1.

Some embodiments of the disclosed method and MIPs may result in at least 70% recovery of LPAs, such as from 70-100%, 80-100%, or 90-100% from a sample. The sample may be a biological sample, such as a plasma or serum sample. LPA recovery may be greater when the sample is acidified prior to loading the sample on the SPE cartridge, and the LPAs subsequently are eluted with an alkaline solution comprising a lower alkyl alcohol. In certain examples, LPA loading increased from 75% to 95% by acidifying the sample, and recovery was increased from 60-70% to 90% by eluting with an alkaline methanol solution. Recoveries also may be greater when using the tandem procedure. In some embodiments, the recovery of individual LPA species is at least 80%, such as from 80-100% from 85-100%, from 90-100%, or from 95-100% when the tandem procedure is followed.

In certain embodiments, crosslinking the MIP with a hydrophobic crosslinker, such as divinylbenzene, may provide results similar to the tandem procedure without using a NIP-containing SPE cartridge before loading the sample onto the MIP-containing SPE cartridge. Inclusion of a hydrophobic crosslinker may bind more hydrophobic interfering components, such as PA, sufficiently tightly to reduce or eliminate co-elution with the LPAs. In one such embodiment, a method for providing a lysophosphatidic acid-enriched sample includes combining a sample comprising plasma or serum with a solvent comprising a lower alkyl alcohol and chloroform to form a mixture, separating organic and aqueous layers of the mixture, acidifying the aqueous layer, loading the acidified aqueous layer onto a SPE cartridge containing a MIP comprising a hydrophobic crosslinker, flowing chloroform and subsequently a lower alkyl alcohol through the SPE cartridge, and then flowing an alkaline solution comprising a lower alkyl alcohol through the SPE cartridge, thereby eluting at least a portion of the lysophosphatidic acid species from the SPE cartridge to provide a lysophosphatidic acid-enriched sample.

The method may further include determining a total concentration of LPAs in the sample and/or determining the presence and/or concentration of individual LPA species in the sample. Exemplary methods for determining LPA concentrations are described in WO 2014/144561, which is incorporated herein by reference.

IV. KITS

Kits for preparing LPA-enriched samples are a feature of this disclosure. Embodiments of the kits include at least one MIP as disclosed herein. The MIP may be disposed in a solid phase extraction cartridge.

In some embodiments, the kit further includes a NIP suitable for removing at least some interfering components from a plasma or serum sample. The NIP may be disposed in a solid phase extraction cartridge. Thus, the kit may include a MIP-containing SPE cartridge and a NIP-containing SPE cartridge. In certain embodiments, the NIP is synthesized from the same functional monomers, crosslinkers, and polymerization initiators as the MIP. In other embodiments, the NIP may differ in chemical composition from the MIP. For example, the NIP may be synthesized with a hydrophobic crosslinker (e.g., divinylbenzene) to increase binding of interfering components, such as phosphatidic acid.

In another embodiment, the kit may include the MIP and one or more empty SPE cartridges, and the end user may subsequently fill one or more of the empty SPE cartridges with MIP prior to use. Similarly, the kit may include a NIP and one or more empty cartridges, and the end user may fill one or more of the empty SPE cartridges with NIP prior to use.

The kits may further include instructions for performing the LPA enrichment process. In certain embodiments, the kit further contains one or more control samples of LPAs. The control samples may be provided in solid form or in solution.

V. EXAMPLES

Instruments and Materials:

NMR spectra were recorded on ARX-400 Advance Bruker spectrometer. FTIR spectra were obtained on a ThermoFisher Nicolet iS10 infrared spectrometer (Thermo Scientific, Madison, Wis.) in reflection geometry using a single bounce diamond attenuated total reflectance (ATR) accessory. LPAs were separated on a Luna™ C-8 (50×2 mm, 3 mm) column connected to a guard cartridge with 2.0 to 3.0 mm internal diameters (Phenomenex) in an Accela UHPLC system (Thermo Fisher, San Jose, Calif.). MS data were collected via an LTQ-Orbitrap XL Discovery instrument (San Jose, Calif., USA), equipped with an ESI ion max source.

All phospholipids were purchased from Avanti Polar Lipids (Alabaster, Ala., USA). Hexadecylphosphonic acid, octadecylphosphonic acid, tris(2-aminoethyl)-amine, 2-isocyanatoethyl methacrylate, methacrylic acid (MAA), ethylene glycol dimethacrylate (EGDMA), and 2,2'-azobisisobutyronitrile (AIBN) were purchased from Sigma-Aldrich (USA). EGDMA was purified by distillation in vacuo. Human plasma samples were collected by Lampire Biological Laboratories Inc. from female donors, processed to obtain platelet-free plasma, and frozen at −80° C. Empty SPE tubes and fits were purchased from Sigma-Aldrich (USA). HPLC grade methanol, chloroform, and water were purchased from VWR (USA).

Example 1

Monomer Selection and Synthesis

Figure 3:
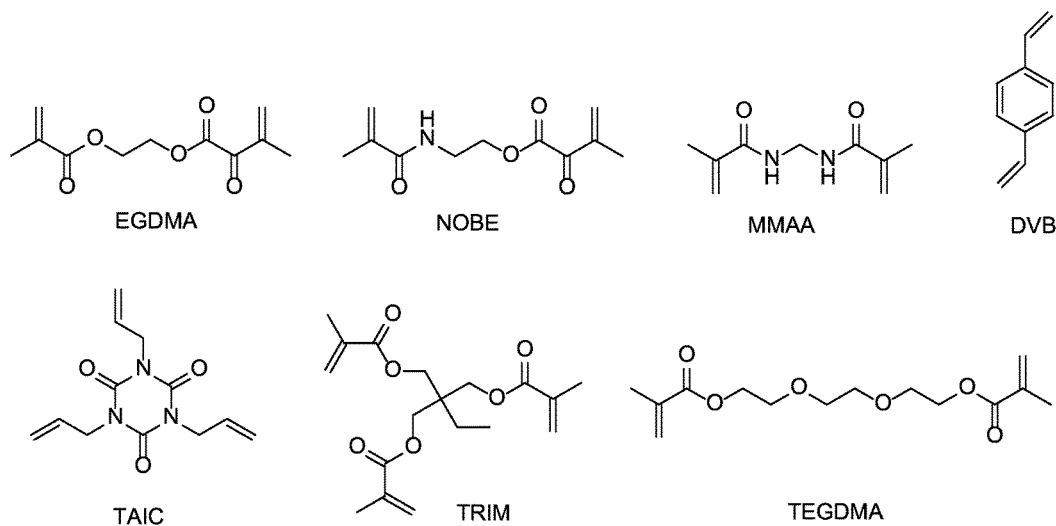
FIG. 3 shows chemical structures of 7 exemplary crosslinking monomers.

Functional monomers and crosslinking monomers were selected from a virtual library of 22 functional monomers containing functionalities for phosphate binding (FIG. 2) and 7 crosslinking monomers (FIG. 3). The Leapfrog algorithm from Tripos Inc. was used to determine the binding of the functional monomer candidates and target analyte LPA 18:0. Functional monomers with the highest binding score and crosslinking monomers with the lowest binding score were selected as the best candidates for polymer preparation. Monomers 1-4 were synthesized following the protocols in literature as described below. The synthetic schemes are shown in Schemes 1-3.

1. Synthesis of 2-Propenoic acid, 2-methyl-, 18-methyl-8-[2-[[[[2-[(2-methyl-1-oxo-2-propen-1-yl)oxy]ethyl]amino]carbonyl]amino]ethyl]-4,12,17-trioxo-16-oxa-3,5,8,11,13-pentaazanonadec-18-en-1-yl ester

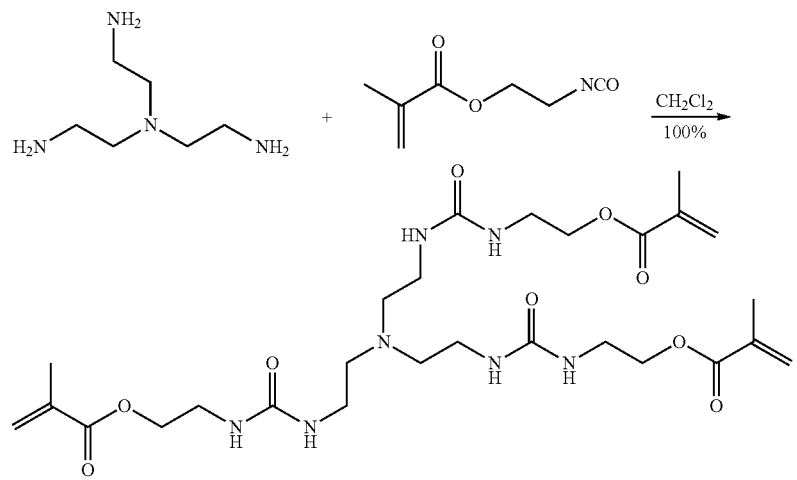

Scheme 1

1

2-Propenoic acid, 2-methyl-, 18-methyl-8-[2-[[[[2-[(2-methyl-1-oxo-2-propen-1-yl)oxy]ethyl]amino]carbonyl]amino]ethyl]-4,12,17-trioxo-16-oxa-3,5,8,11,13-pentaazanonadec-18-en-1-yl ester 1 was synthesized as described in literature (Wu et al., J. Mol. Recognit., 2008, 21:410-8.) Tris(2-aminoethyl)amine (2.2 g, 15.04 mmol) was dissolved in 110 mL dichloromethane and cooled to 0° C. before 2-isocyanatoethyl methacrylate was added in dropwise. The mixture was stirred at room temperature for 4 h. The solvent was evaporated and dried under vacuum. The yield of the product 1 was 9.2 g (100%). $^1$H-NMR and MS data were in agreement with literature. $^1$H NMR (400 MHz, CDCl$_3$): δ6.09 (s, 3H), 6.03 (bs, 3H), 5.80 (bs, 3H), 5.55 (s, 3H), 4.16 (bs, 6H), 3.43 (bs, 6H), 3.12 (bs, 6H), 2.48 (bs, 6H), 1.90 (s, 9H).

$^{13}$C NMR (400 MHz, CDCl$_3$): δ18.40, 38.72, 39.32, 55.36, 64.29, 126.06, 136.17, 159.45, 167.52.

2. Synthesis of 1,1'-(1,3-phenylenebis(methylene)) bis(3-(4-vinylphenyl)urea)

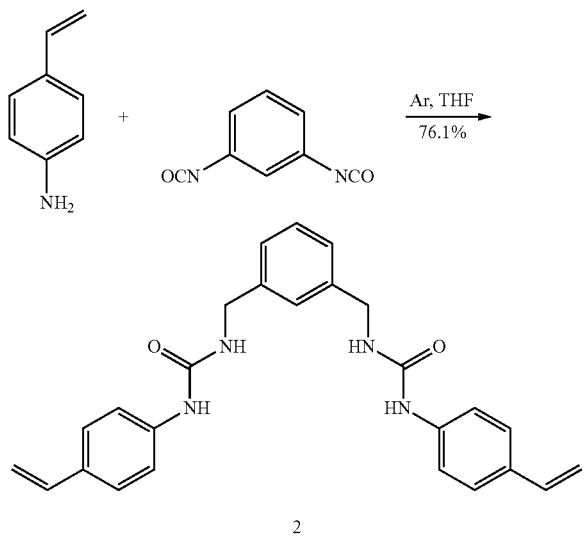

Scheme 2

1,1'-(1,3-phenylenebis(methylene))bis(3-(4-vinylphenyl) urea) 2 was synthesized as described in literature (Emgenbroich et al., *Chemistry*, 2008, 14:9516-29). A solution of 4-aminostyrene (1.19 g, 10 mmol) in anhydrous THF (40 mL) was stirred at room temperature before 1,3-bis(isocyanatemethyl)benzene (0.78 mL, 5 mmol) was added under N$_2$. The reaction was stirred overnight to form a white precipitate. The precipitate was filtered and dried under vacuum to afford the product 2 (1.62 g, 76.1%). $^1$H-NMR (400 MHz, [D6] DMSO): δ4.30 (d, 4H), 5.08 (d, 2H), 5.67 (d, 2H), 6.62 (dd, 4H), 7.15-7.45 (m, 12H), 8.62 ppm (s, 2H).

$^{13}$C-NMR (400 MHz, [D6] DMSO):

δ 42.75, 111.54, 117.58, 125.63, 125.93, 126.59, 128.33, 130.13, 136.33, 140.26, 140.38, 155.03.

3. Synthesis of Vinyl-Benzyl-Cyclen Monomer and Zn (II) Vinyl-Benzyl-Cyclen Monomer Vinyl-benzyl-cyclen monomer 3 and Zn (II) vinyl-benzylcyclen monomer 4 were synthesized as described in literature (Aoki et al., *J. Phys. Org. Chem.*, 2004, 17:489-497).

Scheme 3

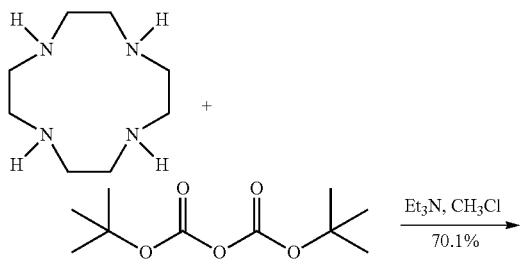

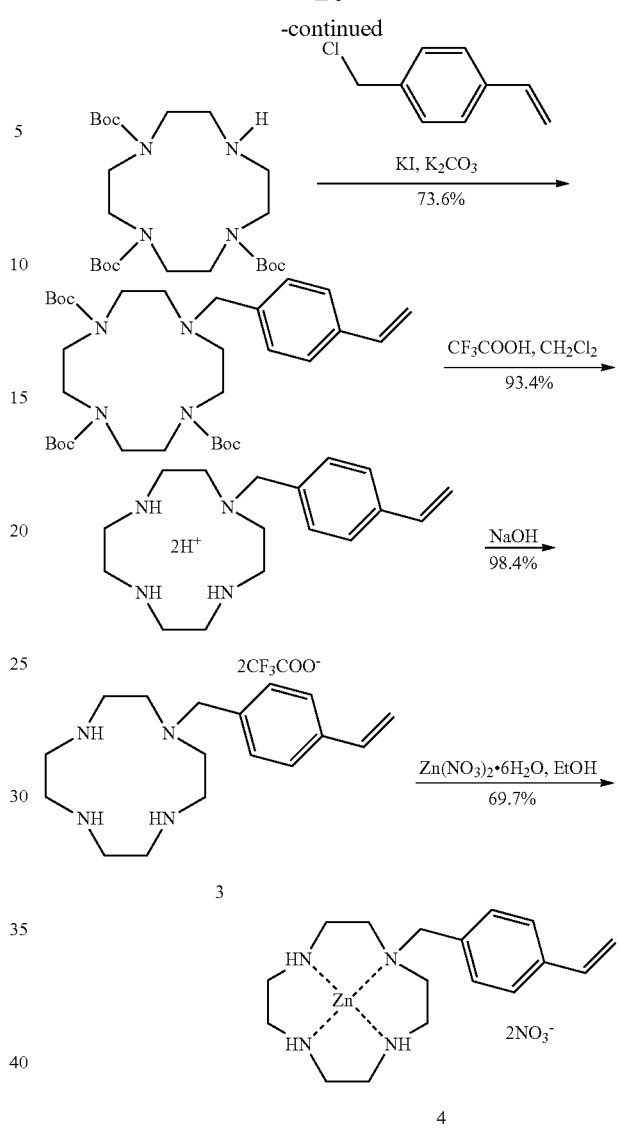

1,4,7-tris(tert-butyloxycarbonyl)-1,4,7,10-tetraazacyclododecane. Di-tert-butyl-dicarbonate (3.59 g, 16.43 mmol) solution in CHCl$_3$ (50 mL) was added dropwise to the solution of cyclen (1.0 g, 5.80 mmol) and triethylamine (1.81 g, 17.88 mmol) in CHCl$_3$ (60 mL) over a 3 hour period. The reaction was stirred for 24 h at room temperature before the solvent was removed under reduced pressure. The crude product was purified via column chromatography using silica gel to afford 1,4,7-tris(tert-butyloxycarbonyl)-1,4,7,10-tetraazacyclododecane as a colorless solid (1.92 g, 70.1%).

1-(4-vinylbenzyl)-4,7,10-tris(tert-butyloxycarbonyl)-1,4, 7,10-tetraazacyclododecane. A solution of 1,4,7-tris(tertbutyloxycarbonyl)-1,4,7,10-tetraazacyclododecane (1.7 g, 3.60 mmol), K$_2$CO$_3$ (0.75 g, 5.4 mmol), KI (0.60 g, 3.6 mmol), and 4-vinylbenzene chloride (0.82 g, 5.40 mol) in MeCN (60 mL) was stirred at 70° C. for 3 h. After the insoluble inorganic salts were removed by filtration, the solvent of the filtrate was evaporated under reduced pressure. The crude product was purified by column chromatography to provide 1-(4-vinylbenzyl)-4,7,10-tris(tert-butyloxycarbonyl)-1,4,7,10-tetraazacyclododecane (1.56 g, 73.6%)

1-(4-vinylbenzyl)-1,4,7,10-tetraazacyclododecane 2TFA salt. Trifluoroacetic acid (12.78 g, 112.1 mmol) was added dropwise to the solution of 1-(4-vinylbenzyl)-4,7,10-tris(tert-butyloxycarbonyl)-1,4,7,10-tetraazacyclododecane (1.20 g, 2.04 mmol) in $CH_2Cl_2$ (130 mL) at 0° C. The reaction was stirred overnight at room temperature. The solvent was evaporated under reduced pressure before toluene (10 mL) was added to the residue and evaporated under reduced pressure. The residue was recrystallized from $Et_2O$-EtOH to afford 1-(4-Vinylbenzyl)-1,4,7,10-tetraazacyclododecane 2TFA salt (0.98 g, 93.4%).

1-(4-vinylbenzyl)-1,4,7,10-tetraazacyclododecane 3. A solution of 1-(4-vinylbenzyl)-1,4,7,10-tetraazacyclododecane 2TFA salt (0.8 g, 1.55 mmol) in water was added to 1M NaOH solution. The aqueous solution was extracted with $CHCl_3$ (50 mL×5) and the organic layers were combined and dried over anhydrous $Na_2SO_4$. The solvent was evaporated under reduced pressure to afford 1-(4-vinylbenzyl)-1,4,7,10-tetraazacyclododecane 3 (0.44 g, 98.4%) $^1$H NMR (400 MHz, $CDCl_3$): δ0.40-0.80 (m, 16H), 1.62 (s, 2H), 3.25 (d, 1H), 3.79 (d, 1H), 4.76 (dd, 1H), 5.30 (d, 2H), 5.44 (d, 2H). $^{13}$C NMR (400 MHz, $CDCl_3$): δ43.69, 44.84, 45.68, 50.28, 57.80, 51.98, 113.46, 125.99, 129.53, 136.23, 136.36, 138.52.

1-(4-vinylbenzyl)-1,4,7,10-tetraazacyclododecane Zn$(NO_3)_2$ salt, $[ZnL_2(NO_3)_2]$ 4. A solution of $Zn(NO_3)_2 \cdot 6H_2O$ (0.23 g) in EtOH (4 mL) was added to a solution of 1-(4-vinylbenzyl)-1,4,7,10-tetraazacyclododecane (0.20 g, 0.70 mmol) in EtOH (0.3 mL) at 60° C. and stirred for 1 h. The solvent was evaporated under reduced pressure and the residue was recrystallized from EtOH—$H_2O$ to afford 1-(4-vinylbenzyl)-1,4,7,10-tetraazacyclododecane Zn $(NO_3)_2$ salt, $[ZnL_2(NO_3)_2]$ 4. (0.23 g, 69.7%) $^1$H NMR (400 MHz, $CDCl_3$): δ0.30-1.1 (m, 16H), 1.80 (s, 2H), 3.19 (d, 1H), 3.73 (d, 1H), 4.62 (dd, 1H), 5.17 (d, 2H), 5.34 (d, 2H). $^{13}$C NMR (400 MHz, $CDCl_3$): δ41.69, 41.81, 43.26, 44.03, 44.15, 48.64, 54.85, 114.47, 125.94, 130.62, 131.22, 135.71, 137.45.

Example 2

Preparation and Characterization of Molecularly Imprinted Polymer and Non-Imprinted Polymer Before the preparation of MIPs using the synthetic functional monomers 1-5, some commercially available functional monomers including 2-vinylpyridine, 4-vinylpyridine, 1-vinylimidazole and 1-allylthiourea were evaluated for use as functional monomers for MIP. However, the selected template molecule octadecylphosphonic acid could not be dissolved with the monomers in chloroform at the desired concentration. Monomer 1 solved this solubility issue by forming a complex with the template, and thus was used as the functional monomer for initial polymer studies.

To study the binding properties of monomer 1, octadecylphosphonic acid was used as the guest molecule. Octadecylphosphonic acid was also selected as the template for imprinting instead of LPA to avoid interfering from potential residue after template extraction. Weakly polar aprotic solvent chloroform was used as the solvent to avoid hydrogen bonding between the solvent and the template or the monomers.

Octadecylphosphonic acid (1.00 g, 2.99 mmol), monomer 1 (1.83 g, 2.99 mmol) and methacrylic acid (0.257 g, 2.99 mmol) were dissolved in 37 mL chloroform and allowed to stand for 60 min for complex formation. EGDMA (11.9 g, 59.8 mmol) was added to the mixture in one portion. The mixture was purged by bubbling nitrogen for 5 min before and after AIBN (0.245 g, 1.49 mmol) was added. Polymerization was carried at 55° C. for 16 h. Polymers were crushed into small pieces before washed with MeOH and extracted in Soxhlet apparatus with MeOH for 48 h before ground and sieved to 63-90 μm. Soxhlet extraction removed 95% of the template molecule, octadecylphosphonic acid, from the imprinted polymer.

Non-imprinted polymer was synthesized using the same protocol, without the presence of template octadecylphosphonic acid.

Figure 4:
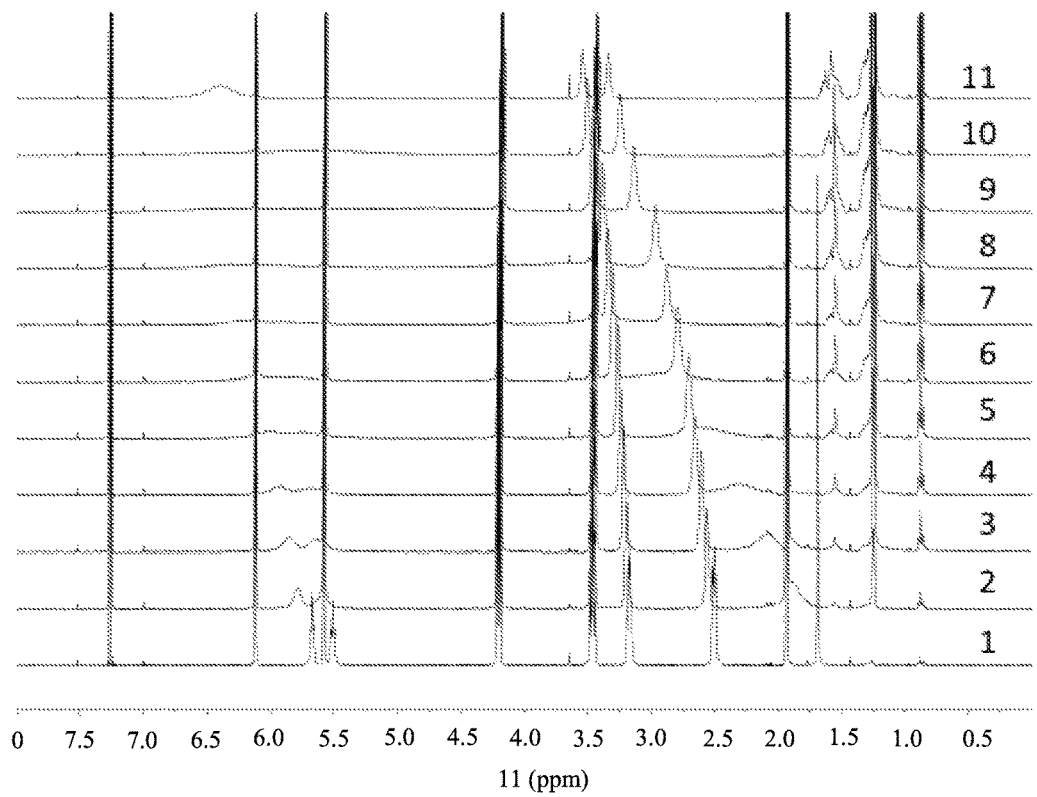
FIG. 4 shows $^1$H NMR titration spectra of monomer 1 and octadecylphosphonic acid. The spectra are numbered according to the mixture numbers in Table 1 of Example 2.
Figure 5:
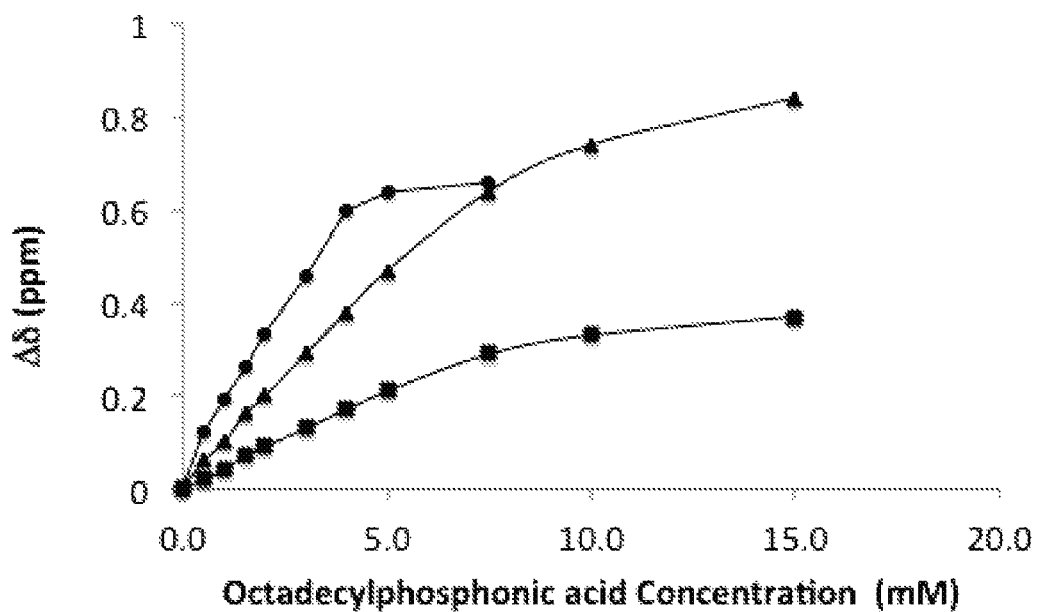
FIG. 5 is a graph of chemical shifts vs. concentration of octadecylphosphonic acid, from the $^1$H NMR titration of monomer 1 with octadecylphosphonic acid. ● represents the N—H proton; ▼ and ■ represent protons of the two adjacent methylene groups.

$^1$H NMR titrations: Stock solutions of the functional monomer 1 (40 mM) and template octadecylphosphonic acid (20 mM) were prepared in $CDCl_3$. The initial concentration of template was 5 mM and was kept constant. The monomer concentrations were 0, 0.5, 1, 1.5, 2, 3, 4, 5, 7.5, 10, 15 mM, respectively. The proton chemical shifts in the urea group and the adjacent methylene groups were monitored. Titration of functional monomer methacrylic acid and template octadecylphosphonic acid was performed using the same protocol. The $^1$H NMR titration experiment in $CDCl_3$ was carried out to determine the association constant of monomer 1 and octadecylphosphonic acid. The titration data and results are shown in Table 1 and FIGS. 4 and 5. With respect to FIG. 5, ● represents the N—H proton; ▲ and ■ represent protons of the two adjacent methylene groups.

Figure 6:
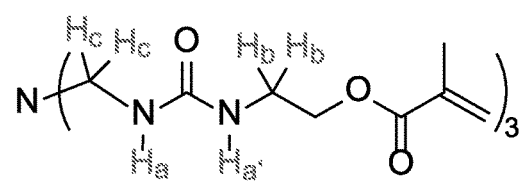
FIG. 6 shows $^1$H NMR titration data of monomer 1 with octadecylphosphonic acid as the guest molecule.
Figure 6:
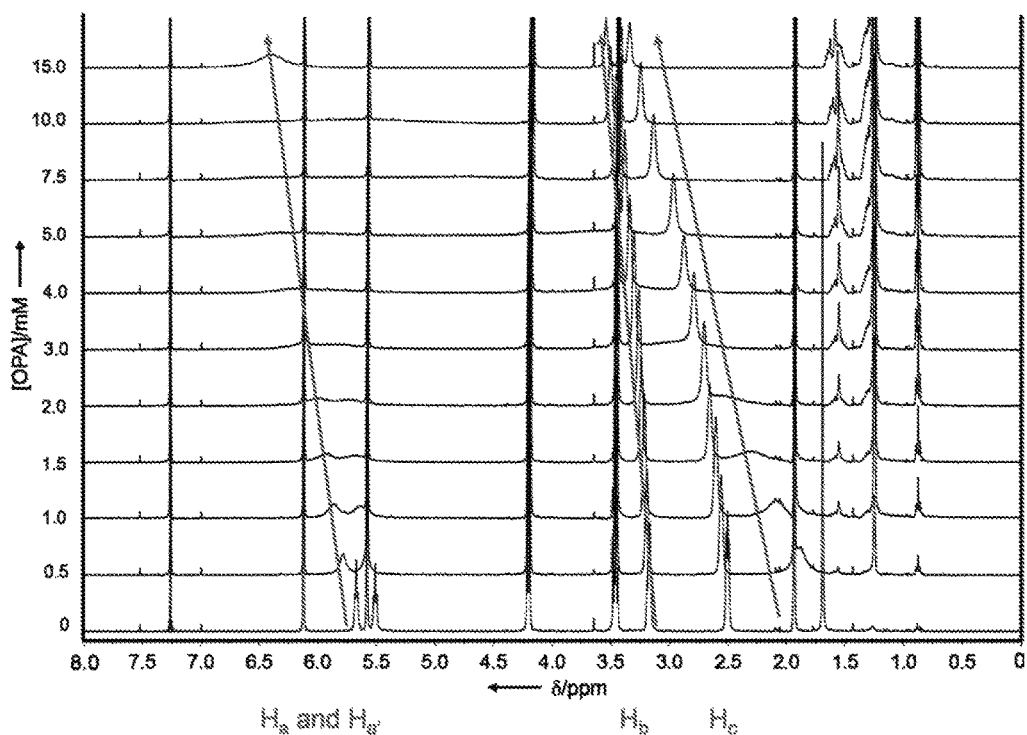

A 1:1 binding model was used to determine the association constant ($K_a$). Results are shown in Table 1 and FIG. 6. Based on the chemical shifts, $K_a$ was calculated to be 83.2 $M^{-1}$. The association constant was calculated by non-linear regression using equation 1. Curve fitting was performed with the program Origin™ 8.0 (OriginLab Corporation).

$$\Delta\delta_{obs}=\Delta\delta_{11}[L]_t/(1+K[L]_t) \quad (1)$$

TABLE 1

Data for $^1$H NMR titration of monomer 1 and octadecylphosphonic acid in $CDCl_3$.

| Mixture No. | Monomer 1 (mM) | Template (mM) | $\Delta\delta_1$ (ppm) $H_a$ and $H_{a'}$ | $\Delta\delta_2$ (ppm) $H_b$ | $\Delta\delta_3$ (ppm) $H_c$ |
|---|---|---|---|---|---|
| 1 | 5 | 0 | 0 | 0 | 0 |
| 2 | 5 | 0.5 | 0.12 | 0.02 | 0.06 |
| 3 | 5 | 1 | 0.19 | 0.04 | 0.1 |
| 4 | 5 | 1.5 | 0.26 | 0.07 | 0.16 |
| 5 | 5 | 2 | 0.33 | 0.09 | 0.2 |
| 6 | 5 | 3 | 0.46 | 0.13 | 0.29 |
| 7 | 5 | 4 | 0.6 | 0.17 | 0.38 |
| 8 | 5 | 5 | 0.64 | 0.21 | 0.47 |
| 9 | 5 | 7.5 | 0.66 | 0.29 | 0.64 |
| 10 | 5 | 10 | — | 0.33 | 0.74 |
| 11 | 5 | 15 | — | 0.37 | 0.84 |
| | | | $K_a = 86.6 M^{-1}$ | $K_a = 82.4 M^{-1}$ | $K_a = 80.6 M^{-1}$ |

Figure 7:
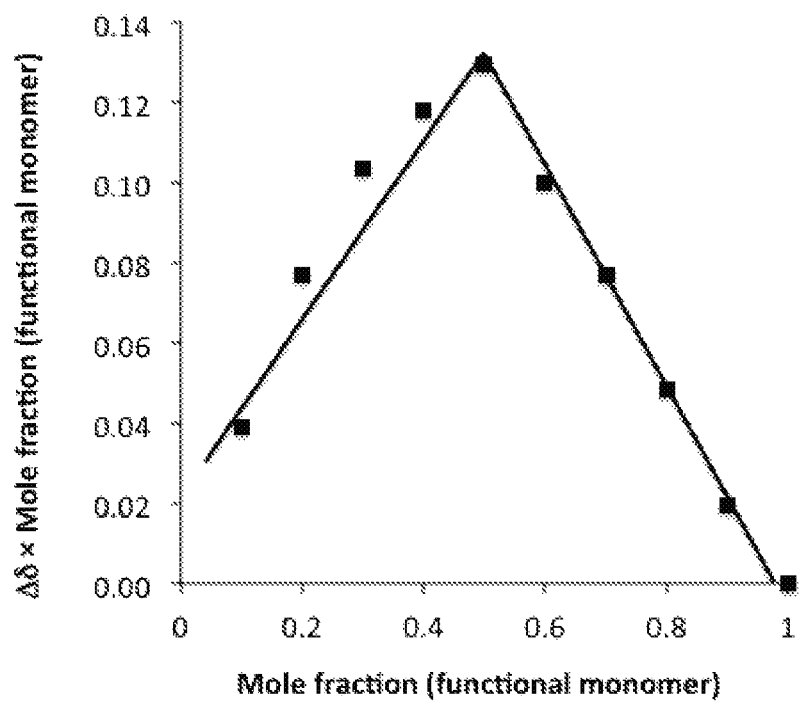
FIG. 7 is a Job plot of monomer 1 with octadecylphosphonic acid in CDCl$_3$ showing a maximum at 0.5 mole fraction of monomer 1.

Job plots for monomers with template: Stock solutions of functional monomers and templates were the same as in $^1$H-NMR titration experiment. The concentration of each solution was 10 mM and the mole ratio of template and monomer 1 was varied from 0/10 to 9/1. The downfield chemical shifts of protons in the urea N—H group and the adjacent methylene protons were monitored (Table 2). Based on the results from the Job plot, the maximum chemical shift was obtained when the mole ratio of monomer 1 and the guest molecule was 1:1. The Job plot is shown in FIG. 7.

TABLE 2

Data for the Job plot performed by $^1$H NMR titration in CDCl$_3$.

| Mixture No. | Monomer 1 (mM) | Template (mM) | Mole fraction (monomer 1) | δ (ppm) | Δδ (ppm) | Δδ × mole fraction |
|---|---|---|---|---|---|---|
| 1 | 10 | 0 | 1 | 3.1683 | 0.0000 | 0.0000 |
| 2 | 9 | 1 | 0.9 | 3.1901 | 2.1683 | 0.0196 |
| 3 | 8 | 2 | 0.8 | 3.2291 | 2.1901 | 0.0486 |
| 4 | 7 | 3 | 0.7 | 3.2784 | 2.2291 | 0.0770 |
| 5 | 6 | 4 | 0.6 | 3.3346 | 2.2784 | 0.0998 |
| 6 | 5 | 5 | 0.5 | 3.4273 | 2.3346 | 0.1295 |
| 7 | 4 | 6 | 0.4 | 3.4633 | 2.4273 | 0.1180 |
| 8 | 3 | 7 | 0.3 | 3.5123 | 2.4633 | 0.1032 |
| 9 | 2 | 8 | 0.2 | 3.5538 | 2.5123 | 0.0771 |
| 10 | 1 | 9 | 0.1 | 3.5563 | 2.5538 | 0.0388 |
| 11 | 0 | 10 | 0 | — | — | — |

Job plot and NMR titration experiments were also done using monomer methacrylic acid as the host and octadecylphosphonic acid as the guest. No chemical shift was observed for the proton in N—H group or the adjacent methylene groups.

Figure 8:
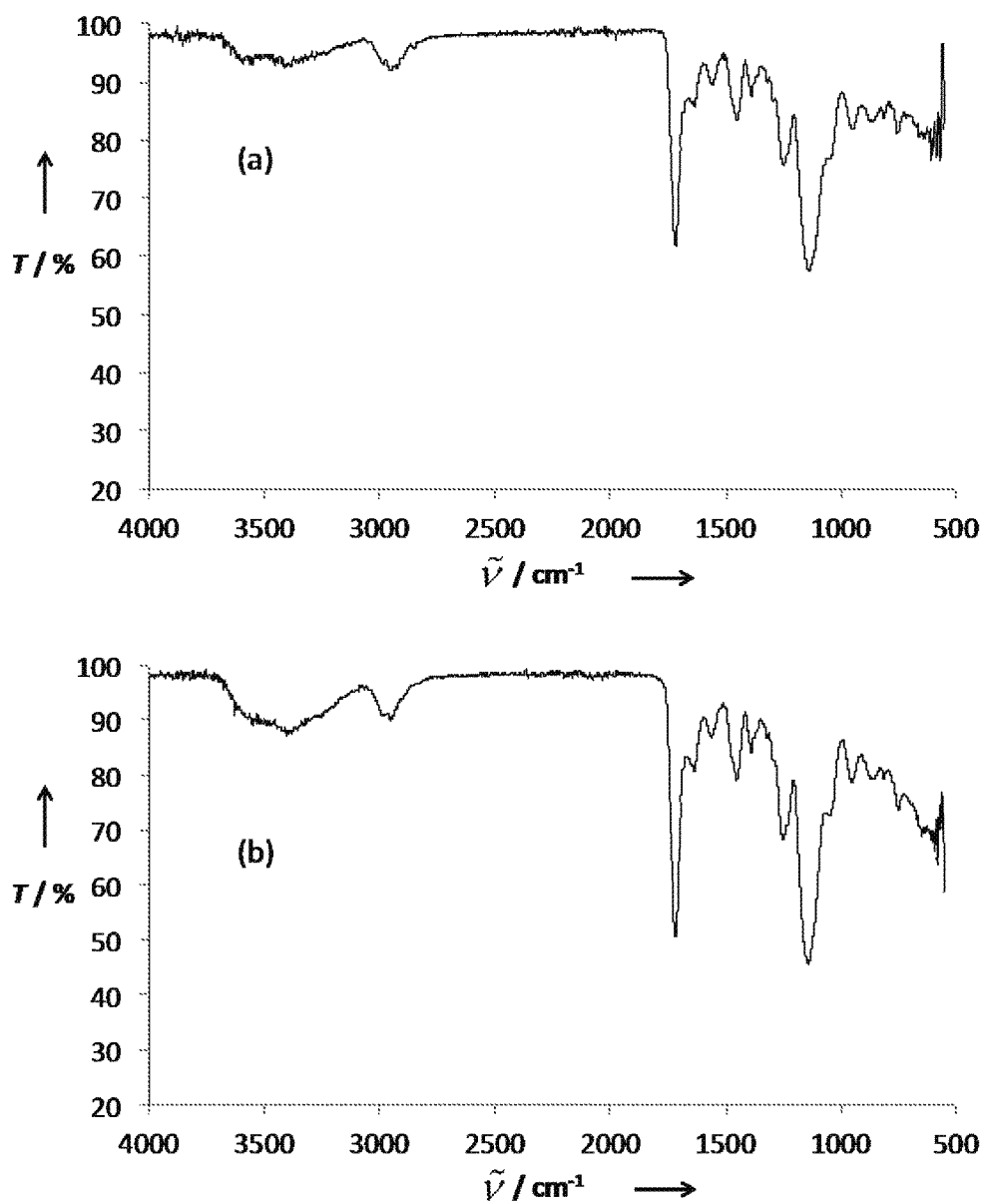
FIG. 8 shows IR spectra of non-imprinted polymer (top panel) and imprinted polymer (bottom panel) after template removal.

Infrared spectroscopy: FTIR spectra of non-imprinted polymer and imprinted polymer after template removal were collected and shown in FIG. 8. The top panel of FIG. 8 is the spectrum of non-imprinted polymer; the bottom panel is the spectrum of the imprinted polymer after template removal. IR of non-imprinted polymer: 3547, 3377, 2961, 1713, 1547, 1445, 1382, 1236, 1126, 1039, 938, 841, 806, 745 cm$^{-1}$. IR of imprinted polymer after template removal: 3531, 3375, 2943, 1714, 1632, 1551, 1448, 1384, 1242, 1137, 1043, 943, 845, 784, 748 cm$^{-1}$. No phosphate group peaks were observed in the spectrum of the imprinted polymer, because 95% of the octadecylphosphonic acid was removed in template extraction step.

Polymer swelling: Dry polymer made with monomer 1 was placed in a 10 mL graduated cylinder and weighed. The weight and volume of the dry polymer were used to calculate the density of the polymer. Excess of chloroform was added and the air bubbles in the polymer were removed by stirring. The polymer was allowed to swell for 24 h. The swelling factor was calculated as the ratio of the volume of the swollen polymers to the dry polymers. The results are shown in Table 3. Although the FTIR spectra of the NIP and MIP are essentially the same since the chemical compositions are the same, the large differences in density and polymer swelling demonstrate that the NIP and MIP clearly have different physical structures.

TABLE 3

Swelling factor and density of non-imprinted and imprinted polymers

| | Non-imprinted polymer | Imprinted polymer |
|---|---|---|
| Density | 0.331 g/mL | 0.647 g/mL |
| Swelling factor | 2.05 | 3.47 |

Example 3

Polymeric Formulations with Monomer 1

Monomer 1 was synthesized and used as the functional monomer in several polymer preparations. The compositions of three representative pairs of non-imprinted and imprinted polymers are shown in Table. 4. All compositions included 16.2 M EGDMA, 0.41 M AIBN, and chloroform as the crosslinking monomer, initiator, and solvent, respectively. The polymers were prepared by bulk polymerization as described in Example 2. Polymers were crushed and subjected to Soxhlet extraction to remove the template, residual monomers, oligomers, and initiator molecules, from the imprinted polymer. After extraction, polymers were ground to a 63-90 μm particle size. SEM microphotographs of the ground non-imprinted polymer (FIG. 9A) and molecularly imprinted polymer (FIG. 9B) show these polymer particles are of irregular shape. LC-MS analysis of the extract shows that the octadecylphosphonic acid (OPA) template was recovered in 95% yield in each formulation.

TABLE 4

NIP and MIP Formulations

| Polymer | Template | Functional monomer 1 | Functional monomer 2 | LPA recovery | PA recovery |
|---|---|---|---|---|---|
| NIP-1 | — | Monomer 1 (0.81M) | — | 39% | — |
| MIP-1 | Octadecylphosphonic acid (0.81M) | Monomer 1 (0.81M) | — | 70% | 72% |
| NIP-2 | — | Monomer 1 (0.81M) | Methacrylic acid (0.81M) | 50% | 10% |
| MIP-2 | Octadecylphosphonic acid (0.81M) | Monomer 1 (0.81M) | Methacrylic acid (0.81M) | 92% | 32% |
| NIP-3 | — | Monomer 1 (0.81M) | 4-vinylpyridine (0.81M) | 72% | 40% |
| MIP-3 | Octadecylphosphonic acid (0.81M) | Monomer 1 (0.81M) | 4-vinylpyridine (0.81M) | 95% | 55% |

LPA control solutions (5 μM) were prepared in methanol and used to evaluate the performance of the MIPs for solid phase extraction. In the first formulation (NIP-1 and MIP-1), monomer 1 was used as the only functional monomer. Similar levels of PA and LPA co-eluted from the MIP. Based on the screening results, 60-80% of each individual LPA was recovered, and 70-80% of PA was bound to and co-eluted with LPA from the MIP.

To increase the recovery and selectivity of the polymer to LPA, one equivalent of methacrylic acid was added in the second formulation (NIP-2 and MIP-2) and 4-vinyl pyridine was added in the third formulation (NIP-3 and MIP-3) to add hydrogen bonding interactions to favor binding of the relatively more polar LPA. With the presence of methacrylic acid in the formulation, the recovery of the relatively less polar PA was lowered by 50%. The recoveries of the individual LPAs were also increased to 70-115%. This is attributed to enhanced H-bonding to the LPA hydroxyl from the methacrylic acid carboxyl group.

In the third formulation (NIP-3 and MIP-3), 4-vinylpyridine was used as the second functional monomer instead of methacrylic acid. The screening results of this formulation showed a similar LPA recovery to Formulation 2, but less selectivity. Thus, MIP-2 was selected and used for further study.

Figure 10:
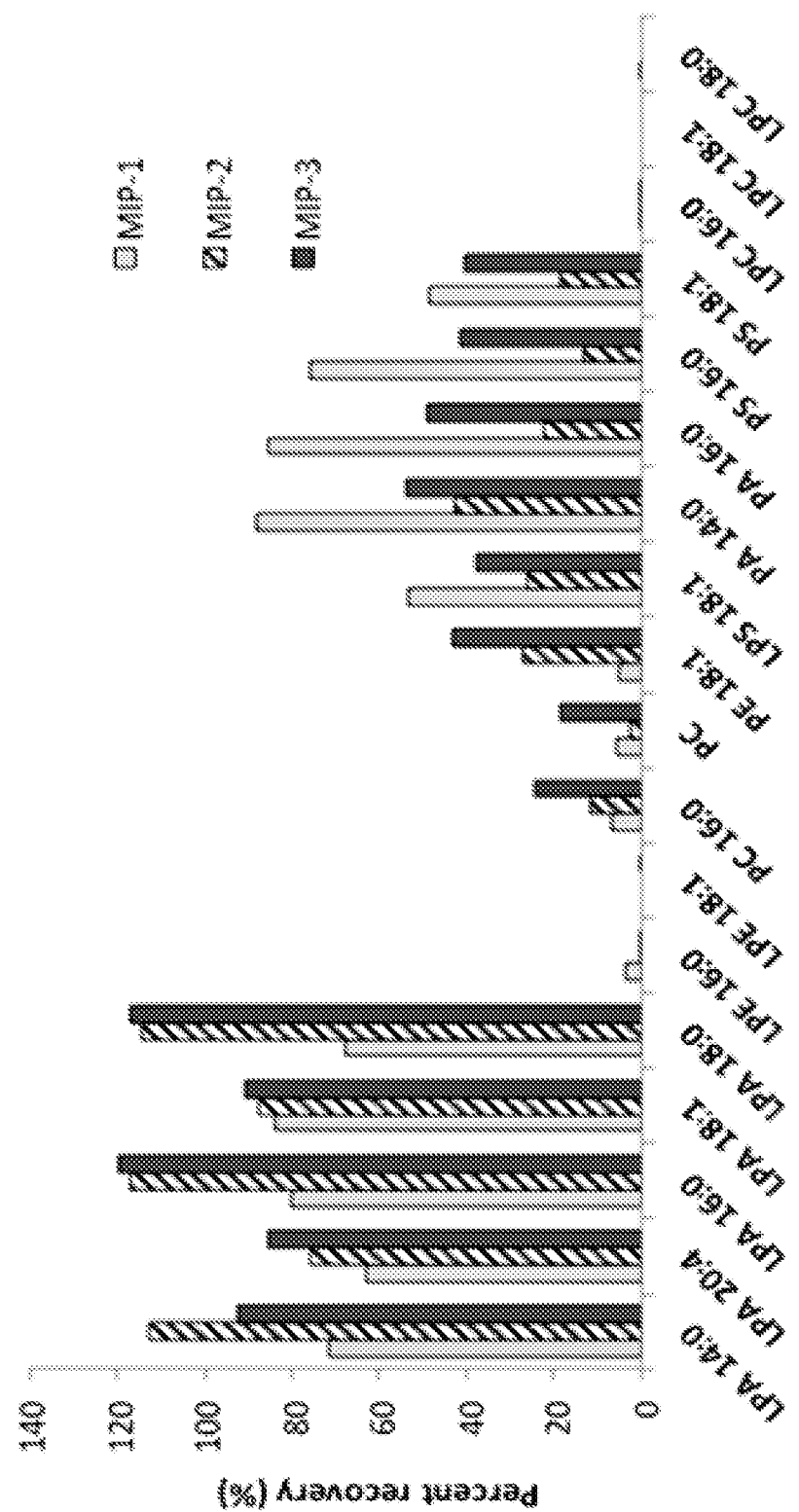
FIG. 10 is a bar chart showing preliminary percent recoveries of several lysophosphatidic acid species and several possible interfering phospholipids using three embodiments of molecularly imprinted polymers prepared with monomer 1.

A performance comparison of the three MIP formulations is shown in FIG. 10. The recoveries of the five major LPA species (14:0, 20:4, 16:0, 18:1, and 18:0) are shown. Recoveries of several possible interferences are also shown: lyso-phosphatidyl ethanolamine (LPE) 16:0, 18:1; phosphatidyl choline (PC) and PC 16:0; phosphatidyl ethanolamine (PE) 18:1; lysophosphatidylserine (LPS) 18:1; phosphatidyl acid (PA) 14:0, 16:0; phosphatidyl serine (PS) 18:1; and lyso-phosphatidylcholine (LPC) 16:0, 18:1, 18:0.

A molecularly imprinted polymer comprising monomer 2 was also prepared and screened (data not shown). The binding of LPA to the polymer prepared from monomer 2 was also quite strong and will be further evaluated.

Example 4

Solid Phase Extraction with Molecularly Imprinted Polymer

The SPE protocol was carried out with control samples of LPA mixtures. In 1:1 $CHCl_3$:MeOH, 75% of the LPA loaded to MIP-2 remained bound. This value was increased to 95% by adding HCOOH to protonate the LPA. To elute the bound LPA, either MeOH or $CHCl_3$ as solvent recovered only 60-70% of the LPA from MIP-2. Addition of 0.05% $NH_4OH$ in MeOH increased the recovery to 90%.

In order to investigate the retention and recovery of other phospholipids, a solution of LPA and PA, along with neutral phospholipids, was prepared. After loading the solution with 1:1 $CHCl_3$:MeOH and HCOOH onto MIP-2, a $CHCl_3$ elution followed by MeOH was found to remove neutral phospholipids, such as LPC and PC, with >99% recovery.

Chloroform followed by methanol was used in a washing step for the removal of neutral phospholipids, such as LPC, PC, etc. Using chloroform for the washing removed only 50% LPC and methanol removed the rest.

Non-imprinted polymers NIP 1-3 were investigated to evaluate the effectiveness of the imprinting method (Table 4, Example 3). Interestingly, NIP-2 showed stronger binding to PA (80% PA retention) than MIP-2 (50% PA retention).

The evaluation demonstrated that the non-imprinted polymer had a stronger binding affinity for PA than the corresponding imprinted polymer under the same loading and elution conditions. For example, about 80% PA was retained in non-imprinted polymer (NIP-3), compared to 50% in imprinted polymer (MIP-3) when samples were loaded in 0.05% formic acid in chloroform and eluted in 0.05% ammonium hydroxide in methanol. This can be interpreted as arising from the differences of selectivity between non-imprinted and imprinted polymers. Non-imprinted polymer has no selectivity in binding phosphate head groups. The double long fatty chains in PA have additional interaction with the hydrophobic groups in the polymer compared to the single chain in LPA. It was determined that optimal LPA recovery and selectivity could be obtained via an SPE method involving sample treatment with NIP-2 (to remove PAs) and MIP-2 (to remove other phospholipids) in tandem.

Example 5

Lysophosphatidic Extraction and Quantification

Figure 11:
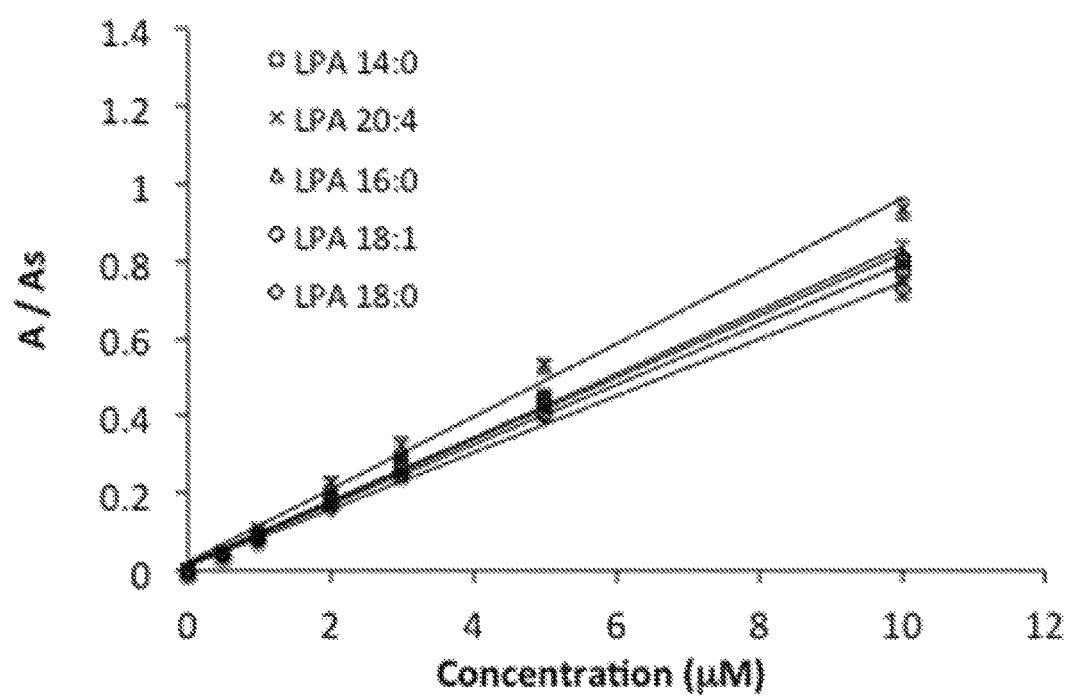
FIG. 11 shows calibration curves of LPA subspecies quantified by LC/MS. The area ratio is the peak area of individual LPA divided by the peak area of the internal standard (LPA 17:0). Data points represent the average of 3 runs.

Mixtures of LPA 14:0, LPA 20:4, LPA 16:0, LPA 18:1 and LPA 18:0 with concentrations ranging from 0.5-10 μM were evaluated by LC/MS with non-natural LPA 17:0 as an internal standard. All LPAs showed linear responses in this range. Statistical values from the calibration curves are shown in Table 5. Calibration curves of the LPA species are shown in FIG. 11. For all LPA species, acceptable correlation factors ($R^2$) were obtained. The limit of detection (LOD) was determined as the amount of analyte that corresponds to three times the signal of the background noise.

TABLE 5

Statistical values from calibration curves for LPA species with LC/MS as the quantification method.

| LPA species | Retention time (min) | Equation | $R^2$ | LOD (μM) |
|---|---|---|---|---|
| 14:0 | 3.78 | y = 0.0804x + 0.0164 | 0.9958 | 0.126 |
| 20:4 | 4.41 | y = 0.0939x + 0.0219 | 0.9941 | 0.153 |
| 16:0 | 4.87 | y = 0.0821x + 0.0156 | 0.9972 | 0.166 |
| 18:1 | 5.32 | y = 0.0775x + 0.0156 | 0.9954 | 0.182 |
| 18:0 | 6.60 | y = 0.0734x + 0.0114 | 0.9967 | 0.225 |

The recoveries of LPA using sequential extraction with NIP-2 and MIP-2 in SPE cartridges were determined using LPA control samples and the results are summarized in Table 6. Solutions comprising 0.05 μM or 2.5 μM LPA mixtures were mixed with 2 mL MeOH—$CHCl_3$ 2:1, vortexed at 2000 rpm for 30 s and incubated at 4° C. for 20 min. After warming to room temperature, the mixture was centrifuged at 2000 rpm for 10 min. The supernatant was decanted and loaded onto a cartridge packed with NIP-2. The NIP-containing cartridge was eluted by 2 mL 0.05% $NH_4OH$ in MeOH. The eluent was acidified to pH 3.0 with concentrated formic acid and loaded to a cartridge packed with 30 mg MIP-2. The MIP-containing cartridge was washed with 2 mL $CHCl_3$, followed by 2 mL MeOH. LPAs were eluted with 3 mL 0.05% $NH_4OH$ in MeOH. The solvent was evaporated under $N_2$ stream, and the residue was reconstituted in 0.2 mL MeOH—$H_2O$ 9:1. Hexadecylphosphonic acid (5 μM) was used as an internal standard instead of octadecylphosphonic acid to eliminate the potential interference from any residue of the template in the MIP. LPA mixtures including 0.5 μM and 2.5 μM of the LPA species were evaluated three times.

TABLE 6

Recoveries of individual LPA species after SPE. (n = 3)

| LPA | Recovery | σ |
|---|---|---|
| 14:0 | 87.1 | 1.5 |
| 20:4 | 86.2 | 1.6 |
| 16:0 | 89.5 | 1.4 |
| 18:1 | 87.6 | 1.5 |
| 17:0 | 85.1 | 1.6 |
| 18:0 | 87.3 | 1.3 |

Example 6

LPA Enrichment of Human Plasma with Molecularly Imprinted Polymer

Commercial human plasma samples and plasma samples spiked with 0.5 μM, 1 μM and 2 μM of each LPA subspecies were used to evaluate the method and determine potential matrix interferences. All samples were prepared and analyzed in triplicate. Human plasma, 600 μL, was mixed with 2 mL MeOH—$CHCl_3$ 2:1, vortexed at 2000 rpm for 30 s and incubated at 4° C. for 20 min. After warming to room temperature, the mixture was centrifuged at 2000 rpm for 10 min. The supernatant was decanted and loaded onto a cartridge packed with NIP-2. The NIP-containing cartridge was eluted by 2 mL 0.05% $NH_4OH$ in MeOH. The eluent was acidified to pH 3.0 with concentrated formic acid and loaded to a cartridge packed with 30 mg MIP-2. The MIP-containing cartridge was washed with 2 mL CHCl$_3$, followed by 2 mL MeOH. LPAs were eluted with 3 mL 0.05% NH$_4$OH in MeOH. The solvent was evaporated under N$_2$ stream, and the residue was reconstituted in 0.2 mL MeOH—H$_2$O 9:1.

LC-ESI/MS procedure for plasma analysis: Samples (10 μL) after the enrichment from SPE step were injected to a Luna™ C-8 (50×2 mm, 3 μm) column at 40° C. Mobile phase MeOH—HCOOH (pH 2.5) 9:1 was delivered at a flow rate of 0.6 mL/min. Ions were created in negative ion mode by setting the sprayer voltage at 3.0 kV and the capillary temperature at 300° C.

Figure 12A:
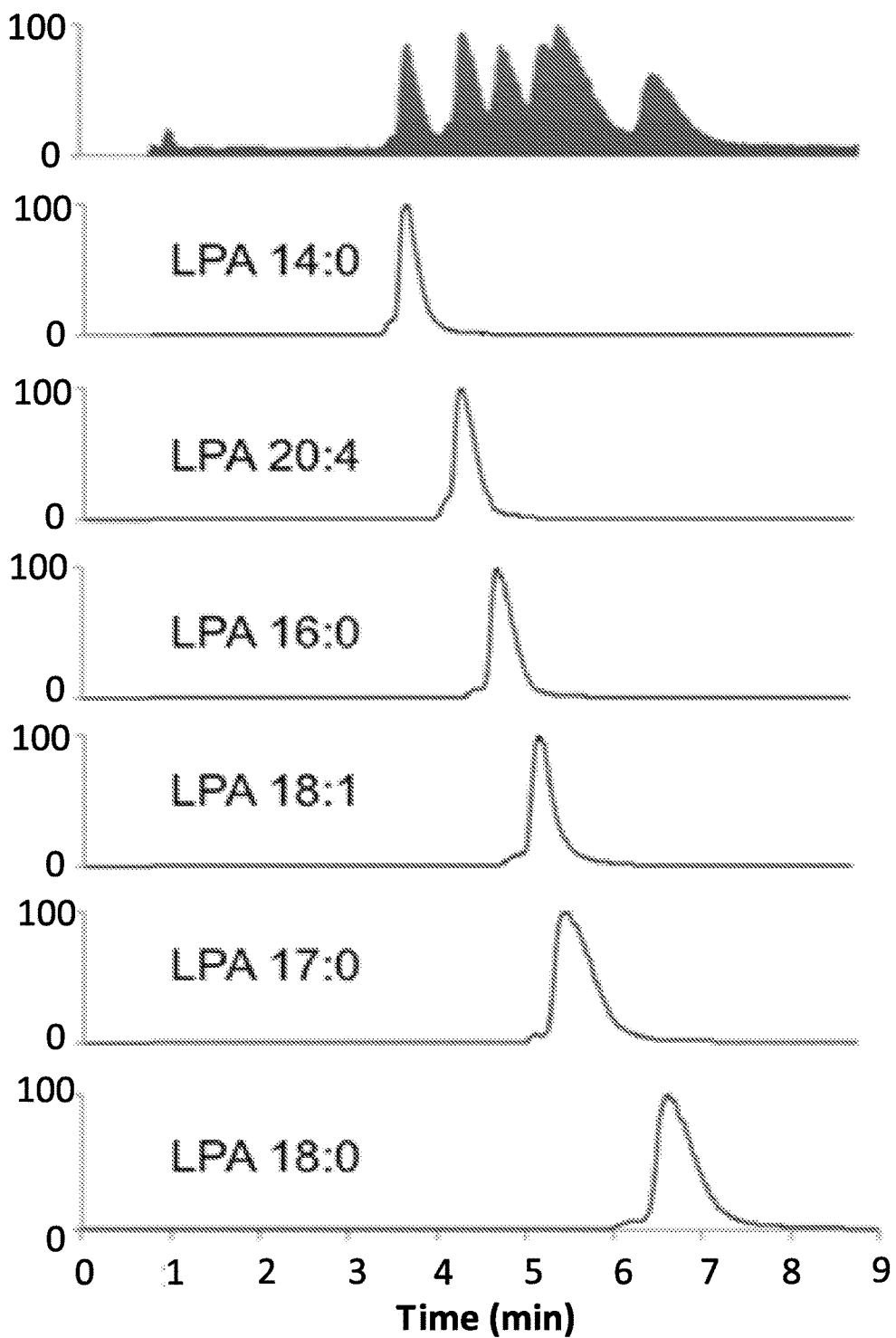
FIGS. 12A and 12B are representative LC-ESI/MS traces of 10 μM standard mixtures of LPAs (FIG. 12A) and a plasma sample (FIG. 12B). Column: Luna™ C-8 (50×2 mm, 3 μm) at 40° C. Injection volume: 10 μL. Mobile phase: 9:1 MeOH—HCOOH (pH 2.5). Flow rate: 0.6 mL/min. Ions were detected in negative ion mode. Sprayer voltage: 3.0 kV and capillary temperature at 300° C.
Figure 12B:
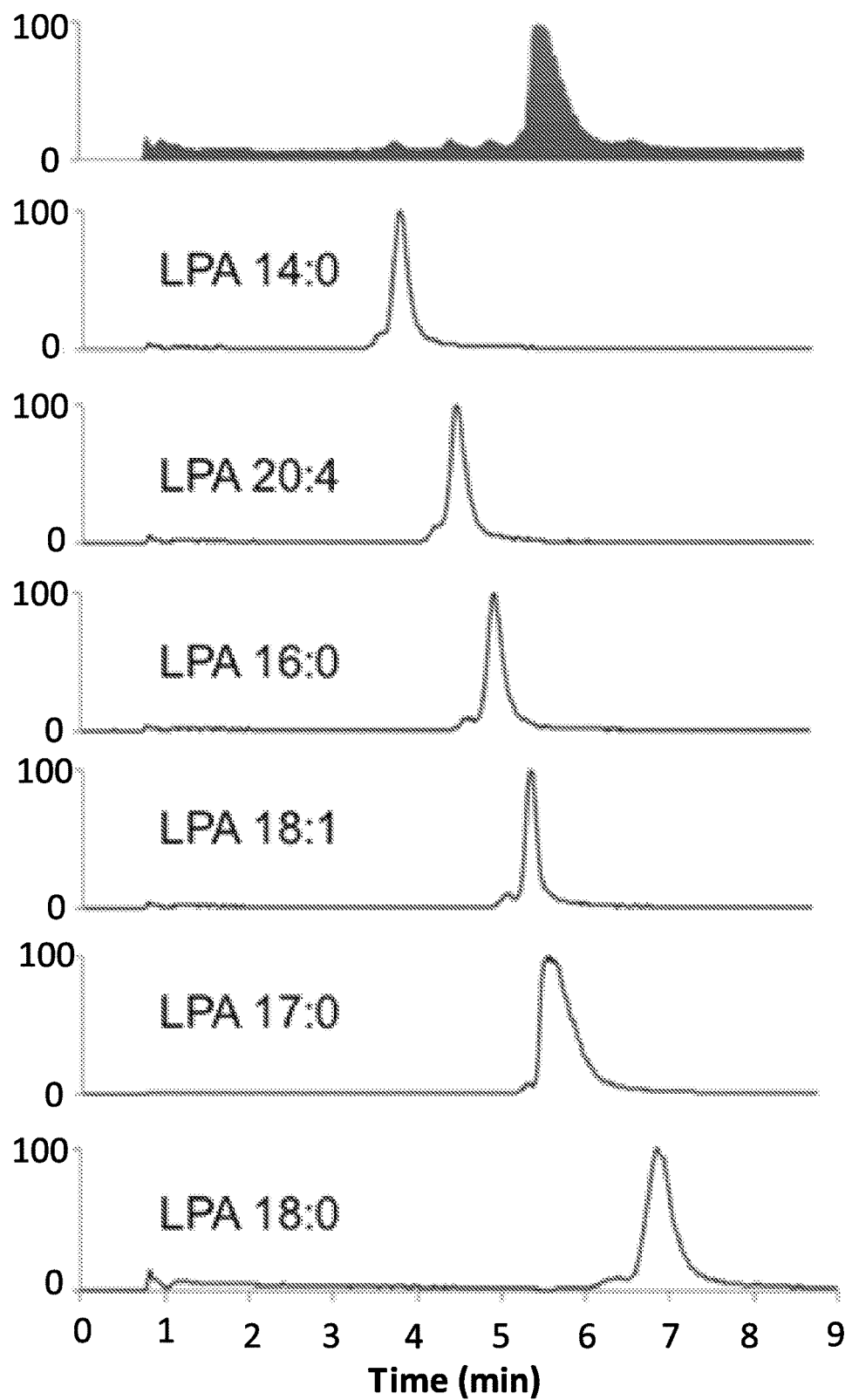

Results of the non-spiked plasma samples and spiked plasma samples are summarized in Table 7; the concentrations shown are μM. Recoveries of the LPA species were excellent, ranging from 94.6% to 105.2% for samples spiked with 1 μM LPAs. Recoveries greater than 100% may be attributable to measurement uncertainty. Acceptable values may range from 70-130% or 80-120%. Representative HPLC traces of LPA control samples (10 μM standard mixtures) and plasma samples are shown in FIGS. 12A and 12B, respectively.

TABLE 7

Results for LPA analysis in human plasma using LC-ESI/MS as the quantification method.

| | Non-spiked | | Spiked with 0.5 μM | | | Spiked with 1 μM | | | Spiked with 2 μM | | |
|---|---|---|---|---|---|---|---|---|---|---|---|
| | avg | σ | avg | σ | % rec | avg | σ | % rec | avg | σ | % rec |
| 14:0 | 0.25 | 0.02 | 0.70 | 0.03 | 91.23 | 1.19 | 0.03 | 94.59 | 2.16 | 0.04 | 95.83 |
| 20:4 | 0.23 | 0.02 | 0.74 | 0.01 | 103.10 | 1.25 | 0.06 | 101.84 | 2.26 | 0.02 | 101.44 |
| 16:0 | 0.37 | 0.02 | 0.93 | 0.04 | 111.56 | 1.42 | 0.05 | 105.17 | 2.45 | 0.03 | 103.98 |
| 18:1 | 0.26 | 0.03 | 0.78 | 0.03 | 103.24 | 1.29 | 0.04 | 103.28 | 2.30 | 0.04 | 101.91 |
| 18:0 | 0.34 | 0.01 | 0.87 | 0.02 | 106.34 | 1.36 | 0.05 | 101.70 | 2.39 | 0.22 | 102.62 |
| Total LPA | 1.45 | 0.05 | 4.02 | 0.07 | 103.09 | 6.51 | 0.10 | 101.32 | 11.56 | 0.23 | 101.16 |

To identify non-LPA phospholipids in the plasma extract after SPE with NIP-2 and MIP-2, an LC/MS full scan in negative and positive mode was performed. A mixture of 22 phospholipids was used as the control sample and each was confirmed to be detectable in either negative or positive mode. The plasma sample after tandem extraction was tested using the same method. Signals were compared to the LIPID MAPS Structure Database (LMSD) (Sud et al., *Nucleic Acids Res* 35, D527-32, 2007). No interfering phospholipids except a trace amount of LPC could be detected. Using the presence of LPC 15:0 as the internal standard, the concentrations of LPC 16:0, LPC 18:1 and LPC 18:0 were estimated to be 0.05 μM, 0.01 μM and 0.02 μM, respectively. The levels represent less than 0.1% of the total LPC in human plasma (Takatera et al., *Journal of Chromatography B* 838, 31-36. 2006). This result shows that the solid phase extraction results in 95% pure LPA samples (Wang et al., *Analyst* 38, 6852-6859, 2013).

Overview of Various Aspects and Representative Embodiments

Other aspects and representative embodiments are as follows:

1. A molecularly imprinted polymer, comprising: a plurality of first structural units derived from monomers comprising (a) at least one functional moiety capable of binding to a phosphate group and (b) at least one polymerizable moiety, the molecularly imprinted polymer having a molecular imprint suitable for binding a lysophosphatidic acid, wherein the molecularly imprinted polymer is obtained by: polymerizing the monomers in a solution comprising (i) a solvent, (ii) a guest molecule comprising an anionic head group and a hydrophobic tail portion, (iii) a crosslinker, and (iv) a radical polymerization initiator to produce a polymer containing the guest molecule, and removing the guest molecule from the polymer containing the guest molecule to produce the molecularly imprinted polymer.

2. The molecularly imprinted polymer of paragraph 1, wherein the functional moiety capable of binding to a phosphate group is an amino, —N(H)—C(O)—N(H)—, —N(H)—C(S)—N(H)—, pyridyl, imidazolyl, pyrimidinyl, pyrazinyl, or cyclenyl moiety, or any combination thereof.

3. The molecularly imprinted polymer of paragraph 1 or paragraph 2, wherein at least some of the monomers comprise a plurality of functional moieties capable of binding to a phosphate group.

4. The molecularly imprinted polymer of any one of paragraphs 1-3, wherein the polymerizable moiety comprises a terminal ethenyl group.

5. The molecularly imprinted polymer of any one of paragraphs 1-4, wherein the first structural units are derived from monomers according to one of the following five chemical structures or a combination of two or more thereof:

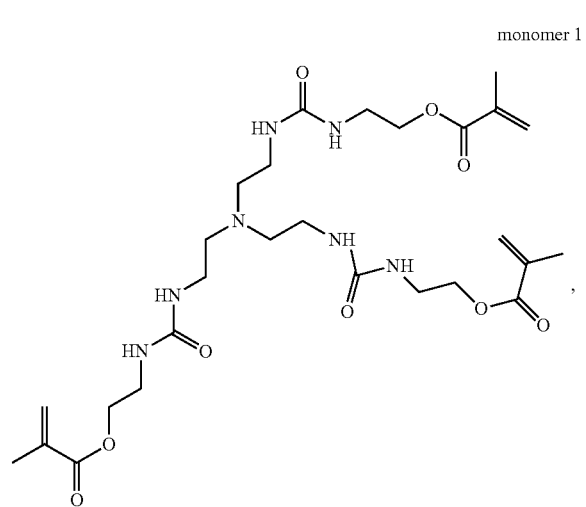

monomer 1

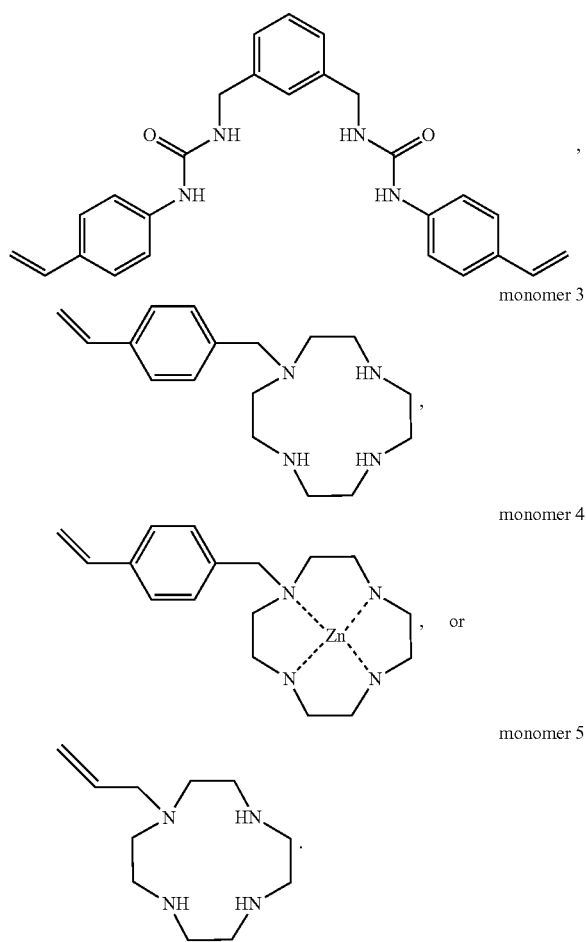

6. The molecularly imprinted polymer of paragraph 5, wherein the first structural units are derived from monomer 1.

7. The molecularly imprinted polymer of any one of paragraphs 1-6, further comprising a plurality of second structural units derived from monomers capable of binding to at least one of a phosphate acid group or a hydroxyl group.

8. The molecularly imprinted polymer of paragraph 7, wherein the second structural units are derived from 2-vinylpyridine, 4-vinylpyridine, 1-vinylimidazole, 4-vinylimidazole, 1-allylthiourea, methacrylic acid, or a combination of two or more thereof.

9. The molecularly imprinted polymer of paragraph 7 or paragraph 8, wherein the first structural unit and the second structural unit are present in a mole ratio from 10:1 to 1:10.

10. The molecularly imprinted polymer of any one of paragraphs 1-9, wherein the guest molecule comprises an anionic head comprising a phosphate or phosphonic acid group.

11. The molecularly imprinted polymer of paragraph 10, wherein the guest molecule comprises a hydrophobic tail comprising a single aliphatic or heteroaliphatic chain.

12. The molecularly imprinted polymer of any one of paragraphs 1-11, wherein the guest molecule is octadecylphosphonic acid.

13. The molecularly imprinted polymer of any one of paragraphs 1-12, wherein the crosslinker comprises ethylene glycol dimethacrylate (EGDMA), divinylbenzene (DVB), tetraethylene glycol dimethacrylate (TEGDMA), N,O-bis-methacrylolyl ethanolamine (NOBE), N,N'-methylenebis-methacrylamide (MMAA), triallyl isocyanurate (TAIL), trimethylolpropane trimethacrylate (TRIM), or a combination of two or more thereof.

14. The molecularly imprinted polymer of any one of paragraphs 5-13, wherein the polymer comprises first structural units derived from monomer 1 and the crosslinker in a mole ratio of 1:5 to 1:50.

15. The molecularly imprinted polymer of any one of paragraphs 6-13, wherein the molecularly imprinted polymer comprises first structural units derived from monomer 1, second structural units derived from methacrylic acid, and EGDMA in a 1:1:20 mole ratio.

16. The molecularly imprinted polymer of any one of paragraphs 1-15, wherein the radical polymerization initiator comprises 2,2'-azobisisobutyronitrile.

17. A method for producing a molecularly imprinted polymer for binding a lysophosphatidic acid, the method comprising: polymerizing monomers comprising (a) at least one functional moiety capable of binding to a phosphate group and (b) at least one polymerizable moiety in a solution comprising (i) a solvent, (ii) a guest molecule comprising an anionic head group and a hydrophobic tail portion, (iii) a crosslinker, and (iv) a radical polymerization initiator to produce a polymer containing the anionic guest molecule; and removing the guest molecule from the polymer containing the guest molecule to produce a molecularly imprinted polymer having a molecular imprint capable of binding lysophosphatidic acid.

18. The method of paragraph 17, wherein removing the guest molecule comprises extracting the guest molecule from the polymer with a lower alkyl alcohol.

19. The method of paragraph 18, wherein extracting comprises Soxhlet extraction with methanol.

20. The method of any one of paragraphs 17-19, wherein the functional moiety capable of binding to a phosphate group is an amino, —N(H)—C(O)—N(H)—, —N(H)—C(S)—N(H)—, pyridyl, imidazolyl, pyrimidinyl, pyrazinyl, or cyclenyl moiety, or any combination thereof.

21. The method of any one of paragraphs 17-20, wherein the monomers comprise a plurality of functional moieties capable of binding to a phosphate group.

22. The method of any one of paragraphs 17-21, wherein the monomers are monomers according to one of the following five chemical structures or a combination of two or more thereof:

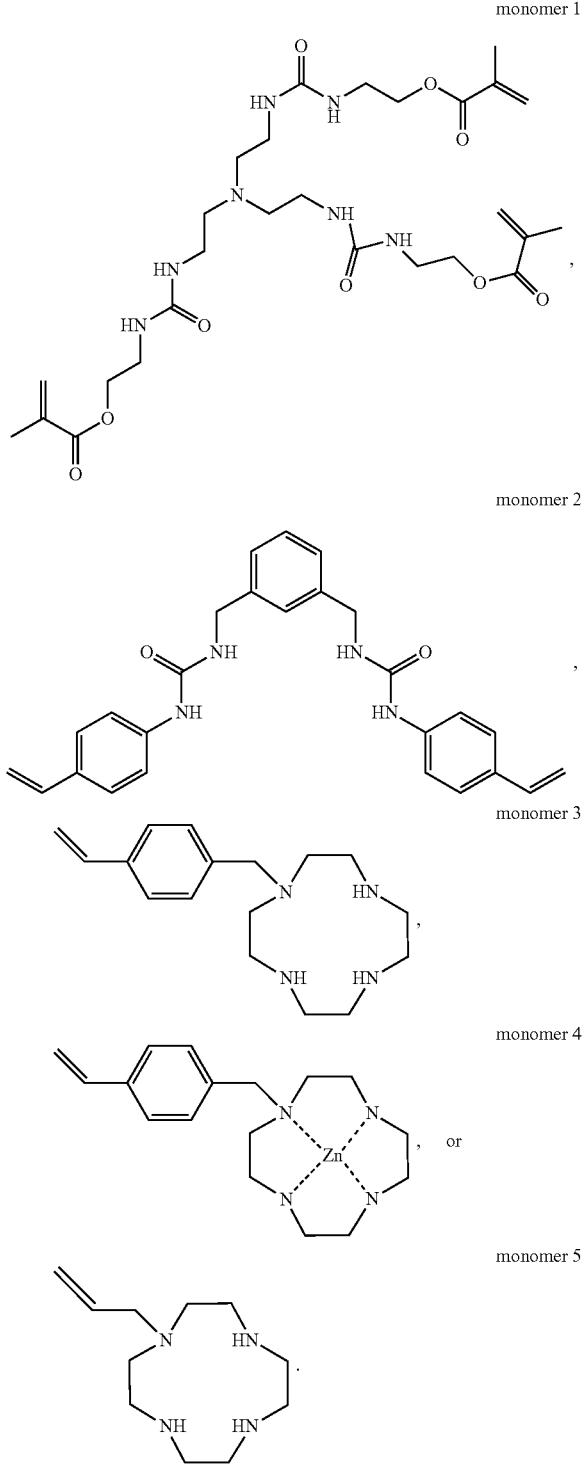

23. The method of any one of paragraphs 17-22, wherein the monomers further comprise 2-vinylpyridine, 4-vinylpyridine, 1-vinylimidazole, 4-vinylimidazole, 1-allylthiourea, methacrylic acid, or a combination of two or more thereof.

24. The method of any one of paragraphs 17-23, wherein the guest molecule comprises an anionic head comprising a phosphate or phosphonic acid group.

25. The method of any one of paragraphs 17-24, wherein the guest molecule is octadecylphosphonic acid.

26. The method of any one of paragraphs 17-25, wherein the crosslinker comprises ethylene glycol dimethacrylate (EGDMA), divinylbenzene (DVB), tetraethylene glycol dimethacrylate (TEGDMA), N,O-bismethacrylolyl ethanolamine (NOBE), N,N'-methylenebismethacrylamide (MMAA), triallyl isocyanurate (TAIL), trimethylolpropane trimethacrylate (TRIM), or a combination of two or more thereof.

27. The method of any one of paragraphs 17-26, wherein the monomers comprise monomer 1 and methacrylic acid in a 1:1 mole ratio.

28. The method of any one of paragraphs 17-27, wherein the radical polymerization initiator comprises 2,2'-azobisisobutyronitrile.

29. A method of preparing a lysophosphatidic acid-enriched sample, comprising: loading a solution comprising one or more lysophosphatidic acid species onto a solid-phase extraction cartridge including a stationary phase comprising a molecularly-imprinted polymer according to any one of paragraphs 1-16 (MIP SPE cartridge); flowing chloroform and subsequently a lower alkyl alcohol through the MIP SPE cartridge; and flowing an alkaline solution comprising a lower alkyl alcohol through the MIP SPE cartridge, thereby eluting at least a portion of the lysophosphatidic acid species from the MIP SPE cartridge to provide a lysophosphatidic acid-enriched sample.

30. The method of paragraph 29, further comprising preparing the solution comprising one or more lysophosphatidic acid species by: combining a sample comprising plasma or serum with a solvent comprising a lower alkyl alcohol and chloroform to form a mixture; separating the mixture to provide a supernatant and a precipitate; acidifying the supernatant to provide the solution comprising one or more lysophosphatidic acid species.

31. The method of paragraph 30, wherein combining the sample comprising plasma or serum with the solvent comprises combining one part of the plasma or serum sample with 3-5 parts of the solvent, the solvent comprising methanol and chloroform in a ratio of 2:1.

32. The method of paragraph 30 or paragraph 31, further comprising: incubating the mixture at 4° C. for a period of time; and warming the mixture to ambient temperature before separating the mixture.

33. The method of any one of paragraphs paragraph 30-32, wherein acidifying the supernatant further comprises: after separating the mixture, loading the supernatant onto a SPE cartridge including a stationary phase comprising a non-imprinted polymer comprising (i) a plurality of first structural units derived from monomers comprising (a) at least one functional moiety capable of binding to a phosphate group and (b) at least one polymerizable moiety (NIP SPE cartridge), and (ii) a crosslinker; flowing an alkaline solution comprising a lower alkyl alcohol through the NIP SPE cartridge to provide an eluent; and acidifying the eluent to provide the solution comprising one or more lysophosphatidic acid species.

34. The method of paragraph 33, wherein the first structural units of the non-imprinted polymer are derived from monomers according to one of the following five chemical structures or a combination of two or more thereof:

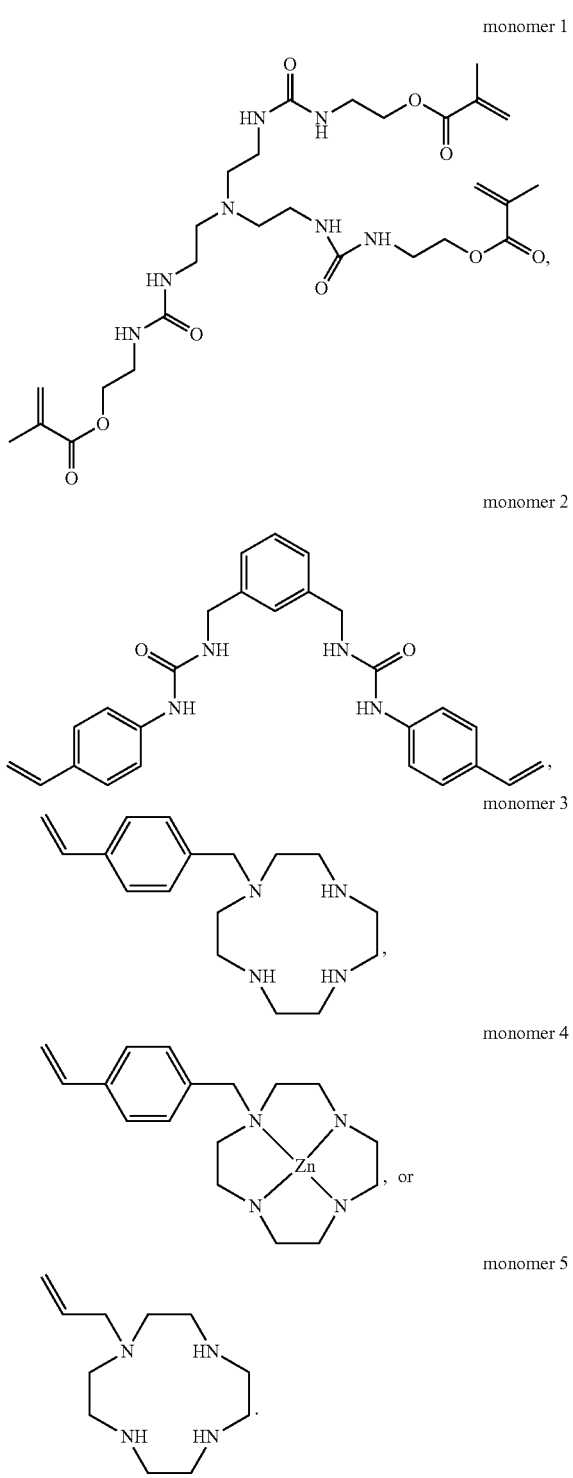

monomer 1
monomer 2
monomer 3
monomer 4
monomer 5

35. The method of paragraph 33 or paragraph 34, wherein the first structural units of the non-imprinted polymer are derived from monomers having the same chemical composition as the monomers from which the first structural units of the molecularly imprinted polymer are derived.

36. The method of any one of paragraphs 33-35, wherein the crosslinker of the non-imprinted polymer comprises ethylene glycol dimethacrylate (EGDMA), divinylbenzene (DVB), tetraethylene glycol dimethacrylate (TEGDMA), N,O-bismethacrylolyl ethanolamine (NOBE), N,N'-methylenebismethacrylamide (MMAA), triallyl isocyanurate (TAIL), trimethylolpropane trimethacrylate (TRIM), or a combination of two or more thereof.

37. The method of any one of paragraphs 33-36, wherein flowing an alkaline solution comprising a lower alkyl alcohol through the NIP SPE cartridge comprises flowing 0.05 wt % $NH_4OH$ in methanol through the NIP SPE cartridge.

38. The method of any one of paragraphs 33-37, wherein acidifying the eluent comprises adding concentrated formic acid to provide a pH within a range of 1-5.

39. The method of any one of paragraphs 29-38, wherein flowing chloroform and subsequently a lower alkyl alcohol through the MIP SPE cartridge comprises flowing chloroform and subsequently methanol through the MIP SPE cartridge.

40. The method of any one of paragraphs 29-39, wherein flowing an alkaline solution comprising a lower alkyl alcohol through the subsequent SPE cartridge comprises flowing 0.05 wt % $NH_4OH$ in methanol through the subsequent SPE cartridge.

41. The method of any one of paragraphs 29-40, further comprising: evaporating solvent from the lysophosphatidic acid-enriched sample to form a dry residue comprising the lysophosphatidic acid species; and dissolving the dry residue in a solvent.

42. The method of paragraph 41, wherein the solvent is 9:1 methanol:$H_2O$.

43. The method of any one of paragraphs 30-42, further comprising determining a total concentration of lysophosphatidic acid species in the sample comprising plasma or serum.

44. The method of paragraph 41 or paragraph 42, further comprising: separating lysophosphatidic acid species in the lysophosphatidic acid-enriched sample using a reversed-phase high-performance liquid chromatography (HPLC) column; and detecting individual lysophosphatidic acid species as or after the separated lysophosphatidic acid species exit the reversed-phase HPLC column.

45. The method of paragraph 44, wherein the lysophosphatidic acid-enriched sample was prepared from a sample comprising plasma or serum, the method further comprising determining a concentration of individual lysophosphatidic acid species in the sample comprising plasma or serum.

46. A kit comprising at least one molecularly imprinted polymer according to any one of paragraphs 1-16.

47. The kit of paragraph 46, wherein the molecularly imprinted polymer is disposed within a solid phase extraction cartridge.

48. The kit of paragraph 46 or paragraph 47, further comprising a non-imprinted polymer comprising (i) a first structural unit derived from monomers comprising (a) at least one functional moiety capable of binding to a phosphate group and (b) at least one polymerizable moiety, and (ii) a crosslinker.

49. The kit of paragraph 48, wherein the non-imprinted polymer is disposed within a solid phase extraction cartridge.

50. The kit of paragraph 48 or paragraph 49, wherein the first structural unit of the non-imprinted polymer is prepared from monomers having the same chemical composition as the monomers from which the first structural unit of the molecularly imprinted polymer is derived.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A molecularly imprinted polymer, comprising:
a plurality of first structural units derived from monomers comprising (a) at least one functional moiety selected from an amino, —N(H)C(O)N(H), —N(H)—C(S)—N(H)—, pyridyl, imidazolyl, pyrimidinyl, pyrazinyl, or cyclenyl moiety, or any combination thereof, and (b) at least one polymerizable moiety, the molecularly imprinted polymer having a molecular imprint having a size and shape complementary to a lysophosphatidic acid, wherein the molecularly imprinted polymer is obtained by:
polymerizing the monomers in a solution comprising (i) a solvent, (ii) a guest molecule comprising an anionic head group comprising a phosphate or phosphonic acid group and a hydrophobic tail portion comprising a single hydrocarbon chain with a length of from 12-24 carbons, wherein the guest molecule is not a lysophosphatidic acid, (iii) a crosslinker, and (iv) a radical polymerization initiator to produce a polymer containing the guest molecule, and
removing the guest molecule from the polymer containing the guest molecule to produce the molecularly imprinted polymer.

2. The molecularly imprinted polymer of claim 1, wherein:
(a) at least some of the monomers comprise a plurality of functional moieties capable of binding to a phosphate group; or
(b) the polymerizable moiety comprises a terminal ethenyl group; or
(c) both (a) and (b).

3. The molecularly imprinted polymer of claim 1, wherein the first structural units are derived from monomers according to one of the following five chemical structures or a combination of two or more thereof:

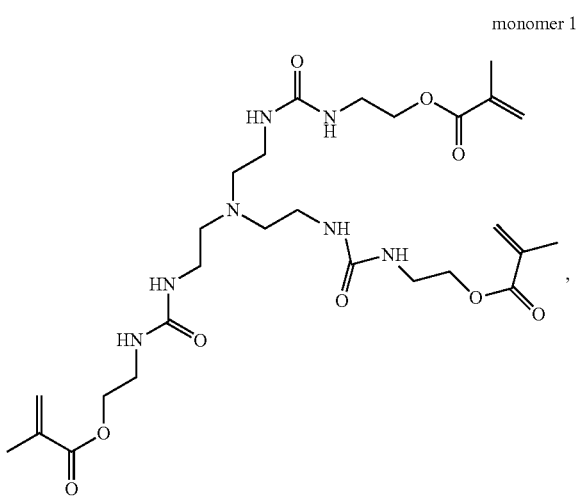

monomer 1

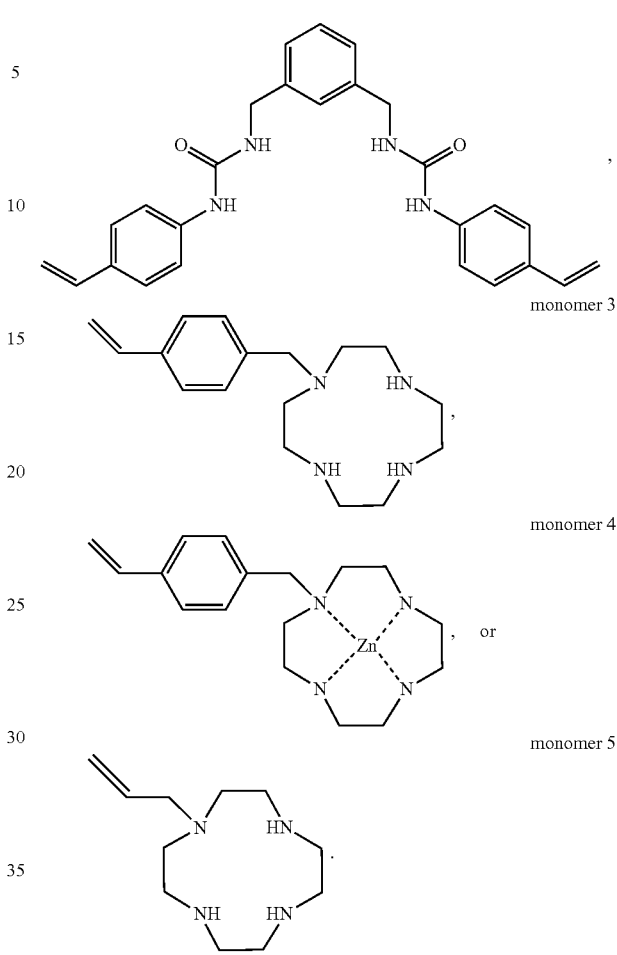

monomer 2 monomer 3 monomer 4 monomer 5

4. The molecularly imprinted polymer of claim 1, further comprising a plurality of second structural units derived from 2 vinylpyridine, 4-vinylpyridine, 1-vinylimidazole, 4-vinylimidazole, 1-allylthiourea, methacrylic acid, or a combination of two or more thereof.

5. The molecularly imprinted polymer of claim 4, wherein the first structural unit and the second structural unit are present in a mole ratio from 10:1 to 1:10.

6. The molecularly imprinted polymer of claim 1, wherein:
(a) the crosslinker comprises ethylene glycol dimethacrylate (EGDMA), divinylbenzene (DVB), tetraethylene glycol dimethacrylate (TEGDMA), N,O-bismethacrylolyl ethanolamine (NOBE), N,N'-methylenebismethacrylamide (MMAA), triallyl isocyanurate (TAIL), trimethylolpropane trimethacrylate (TRIM), or a combination of two or more thereof; or
(b) the radical polymerization initiator comprises 2,2'-azobisisobutyronitrile; or
(c) both (a) and (b).

7. The molecularly imprinted polymer of claim 3, wherein:
(a) the polymer comprises first structural units derived from monomer 1 and the crosslinker in a mole ratio of 1:5 to 1:50; or
(b) the molecularly imprinted polymer comprises first structural units derived from monomer 1, second structural units derived from methacrylic acid, and EGDMA in a 1:1:20 mole ratio.

8. The molecularly imprinted polymer of claim 1, wherein the first structural units are derived from monomer 1, monomer 2, or a combination thereof:

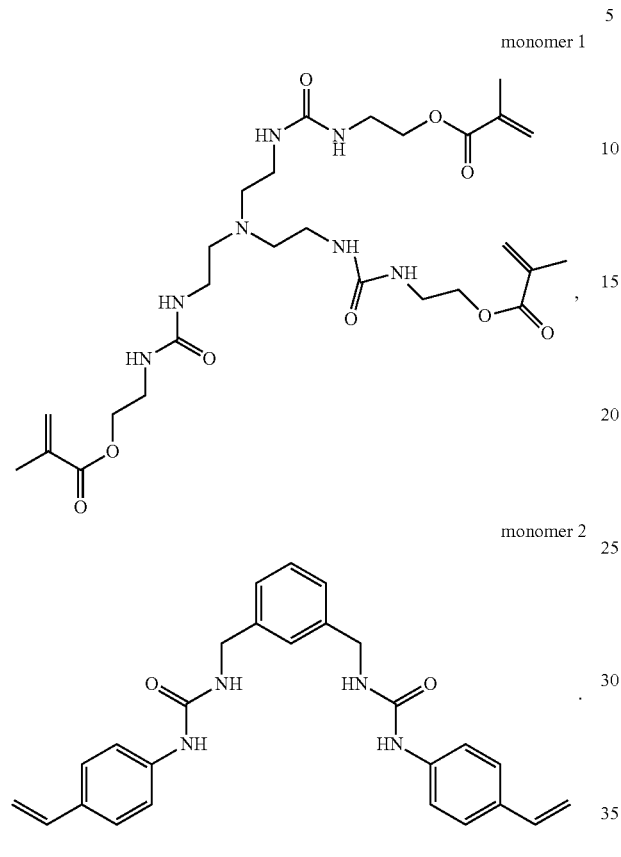

9. A molecularly imprinted polymer, comprising:
a plurality of first structural units derived from monomers comprising (a) at least one functional moiety selected from an amino, —N(H)C(O)N(H), —N(H)—C(S)—N(H)—, pyridyl, imidazolyl, pyrimidinyl, pyrazinyl, or cyclenyl moiety, or any combination thereof, and (b) at least one polymerizable moiety, the molecularly imprinted polymer having a molecular imprint having a size and shape complementary to a lysophosphatidic acid, wherein the molecularly imprinted polymer is obtained by:
polymerizing the monomers in a solution comprising (i) a solvent, (ii) a guest molecule, wherein the guest molecule is octadecylphosphonic acid, (iii) a crosslinker, and (iv) a radical polymerization initiator to produce a polymer containing the guest molecule, and
removing the guest molecule from the polymer containing the guest molecule to produce the molecularly imprinted polymer.

10. A method for producing a molecularly imprinted polymer for binding a lysophosphatidic acid, the method comprising:
polymerizing monomers comprising (a) at least one functional moiety selected from an amino, —N(H)—C(O)—N(H)—, —N(H)—C(S)—N(H)—, pyridyl, imidazolyl, pyrimidinyl, pyrazinyl, or cyclenyl moiety, or any combination thereof, and (b) at least one polymerizable moiety in a solution comprising (i) a solvent, (ii) a guest molecule comprising an anionic head group comprising a phosphate or phosphonic acid group and a hydrophobic tail portion comprising a single hydrocarbon chain with a length of from 12-24 carbons, wherein the guest molecule is not a lysophosphatidic acid, (iii) a crosslinker, and (iv) a radical polymerization initiator to produce a polymer containing the anionic guest molecule; and
removing the guest molecule from the polymer containing the guest molecule to produce a molecularly imprinted polymer having a molecular imprint having a size and shape complementary to lysophosphatidic acid.

11. The method of claim 10, wherein the monomers are monomers according to one of the following five chemical structures or a combination of two or more thereof:

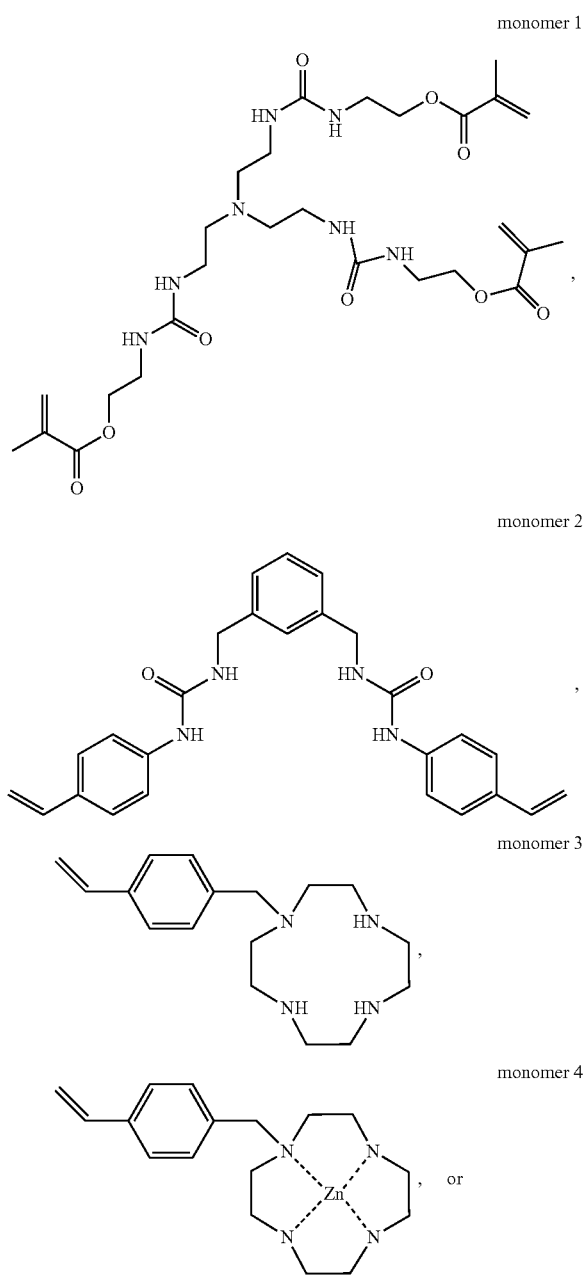

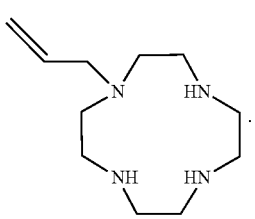

monomer 5

12. The method of claim 10, wherein the monomers further comprise 2-vinylpyridine, 4-vinylpyridine, 1-vinylimidazole, 4-vinylimidazole, 1-allylthiourea, methacrylic acid, or a combination of two or more thereof.

13. A method of preparing a lysophosphatidic acid-enriched sample, comprising:

loading a solution comprising one or more lysophosphatidic acid species onto a solid-phase extraction cartridge including a stationary phase comprising a molecularly-imprinted polymer according to claim 1 (MIP SPE cartridge);

flowing chloroform and subsequently a lower alkyl alcohol through the MIP SPE cartridge; and flowing an alkaline solution comprising a lower alkyl alcohol through the MIP SPE cartridge, thereby eluting at least a portion of the lysophosphatidic acid species from the MIP SPE cartridge to provide a lysophosphatidic acid-enriched sample.

14. The method of claim 13, further comprising preparing the solution comprising one or more lysophosphatidic acid species by:

combining a sample comprising plasma or serum with a solvent comprising a lower alkyl alcohol and chloroform to form a mixture;

separating the mixture to provide a supernatant and a precipitate;

acidifying the supernatant to provide the solution comprising one or more lysophosphatidic acid species.

15. The method of claim 14, wherein acidifying the supernatant further comprises:

after separating the mixture, loading the supernatant onto a SPE cartridge including a stationary phase comprising a non-imprinted polymer comprising (i) a plurality of first structural units derived from monomers comprising (a) at least one functional moiety capable of binding to a phosphate group and (b) at least one polymerizable moiety (NIP SPE cartridge), and (ii) a crosslinker;

flowing an alkaline solution comprising a lower alkyl alcohol through the NIP SPE cartridge to provide an eluent; and acidifying the eluent to provide the solution comprising one or more lysophosphatidic acid species.

16. The method of claim 15, wherein the first structural units of the non-imprinted polymer are derived from monomers according to one of the following five chemical structures or a combination of two or more thereof:

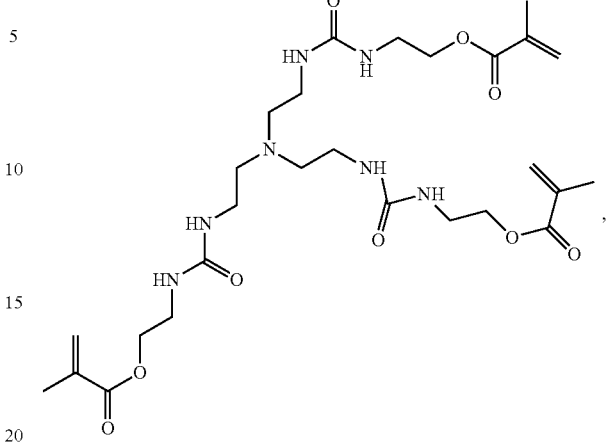

monomer 1

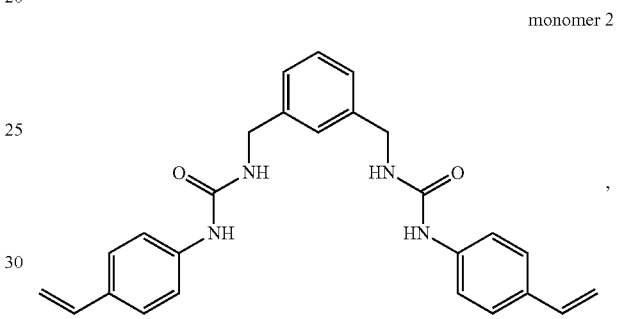

monomer 2

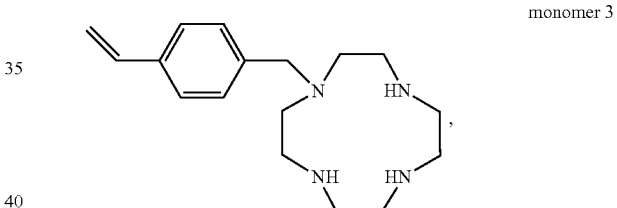

monomer 3

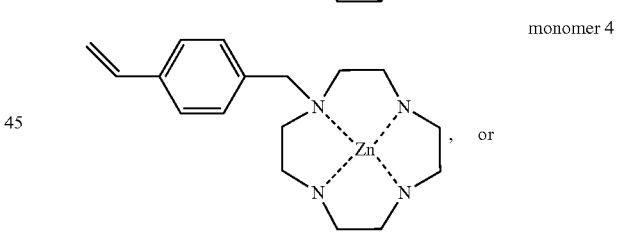

monomer 4

, or

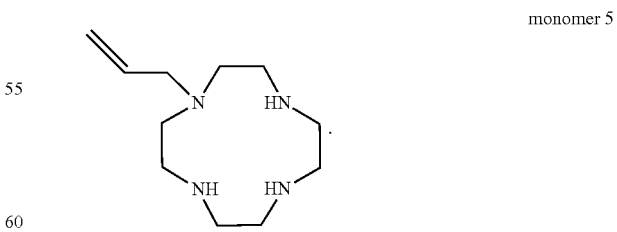

monomer 5

17. The method of claim 15, wherein the first structural units of the non-imprinted polymer are derived from monomers having the same chemical composition as the monomers from which the first structural units of the molecularly imprinted polymer are derived.

18. The method of claim 15, wherein:
(a) flowing an alkaline solution comprising a lower alkyl alcohol through the NIP SPE cartridge comprises flowing 0.05 wt % $NH_4OH$ in methanol through the NIP SPE cartridge;
(b) acidifying the eluent comprises adding concentrated formic acid to provide a pH within a range of 1-5;
(c) flowing chloroform and subsequently a lower alkyl alcohol through the MIP SPE cartridge comprises flowing chloroform and subsequently methanol through the MIP SPE cartridge;
(d) flowing an alkaline solution comprising a lower alkyl alcohol through the subsequent SPE cartridge comprises flowing 0.05 wt % $NH_4OH$ in methanol through the subsequent SPE cartridge; or
(e) any combination of (a)-(d).

19. The method of claim 14, further comprising determining a total concentration of lysophosphatidic acid species in the sample comprising plasma or serum by:
separating lysophosphatidic acid species in the lysophosphatidic acid-enriched sample using a reversed-phase high-performance liquid chromatography (HPLC) column; and
detecting individual lysophosphatidic acid species as or after the separated lysophosphatidic acid species exit the reversed-phase HPLC column.

20. The method of claim 19, further comprising determining a concentration of individual lysophosphatidic acid species in the sample comprising plasma or serum.

21. The method of claim 13, wherein:
(a) the molecularly imprinted polymer comprises first structural units derived from monomer 1 and the crosslinker in a mole ratio of 1:5 to 1:50; or
(b) the molecularly imprinted polymer comprises first structural units derived from monomer 1, second structural units derived from methacrylic acid, and EGDMA in a 1:1:20 mole ratio.

22. A kit comprising at least one molecularly imprinted polymer according to claim 1.

* * * * *